United States Patent
Ichikawa et al.

(10) Patent No.: US 8,420,294 B2
(45) Date of Patent: Apr. 16, 2013

(54) SALT AND PHOTORESIST COMPOSITION COMPRISING THE SAME

(75) Inventors: Koji Ichikawa, Osaka (JP); Yukako Anryu, Osaka (JP); Shingo Fujita, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/304,478

(22) Filed: Nov. 25, 2011

(65) Prior Publication Data

US 2012/0135351 A1     May 31, 2012

(30) Foreign Application Priority Data

Nov. 30, 2010  (JP) ................. 2010-266200
Mar. 1, 2011   (JP) ................. 2011-043586

(51) Int. Cl.
| G03F 7/004 | (2006.01) |
| G03F 7/30 | (2006.01) |
| C07C 309/65 | (2006.01) |
| C07C 309/71 | (2006.01) |
| C07D 321/10 | (2006.01) |
| C07D 321/12 | (2006.01) |

(52) U.S. Cl.
USPC ........ 430/270.1; 430/326; 430/330; 430/910; 549/333; 549/340; 549/453; 549/454; 562/100; 562/108; 562/109; 562/113

(58) Field of Classification Search ........... 430/270.1, 430/326, 330, 910; 549/333, 340, 453, 454; 562/100, 108, 109, 113
See application file for complete search history.

(56) References Cited

U.S. PATENT DOCUMENTS

2007/0122750 A1   5/2007  Yamaguchi et al.
2012/0088190 A1*  4/2012  Ichikawa et al. ........... 430/281.1

FOREIGN PATENT DOCUMENTS

JP    2004-59435 A    2/2004

* cited by examiner

*Primary Examiner* — John Chu
(74) *Attorney, Agent, or Firm* — Birch, Stewart, Kolasch & Birch, LLP

(57) ABSTRACT

The present invention provides a salt represented by the formula (I):

$$Z^{1+} \ {}^{-}O_3S-\underset{R^4}{\overset{R^3}{\underset{|}{\overset{|}{C}}}}-X^1-O-\underset{R^1 \ R^2}{\overset{}{\underset{}{\text{(dioxolane)}}}} \quad (I)$$

wherein $R^1$ and $R^2$ independently each represent a C1-C6 alkyl group or $R^1$ and $R^2$ are bonded each other to form a C5-C20 aliphatic ring together with the carbon atom to which they are bonded, $R^3$ and $R^4$ independently each represent a fluorine atom or a C1-C6 perfluoroalkyl group, $X^1$ represents a C1-C17 divalent saturated hydrocarbon group in which one or more —$CH_2$— can be replaced by —O— or —CO— and which may be substituted with one or more fluorine atoms, and $Z^{1+}$ represents an organic counter ion.

8 Claims, No Drawings

SALT AND PHOTORESIST COMPOSITION COMPRISING THE SAME

This nonprovisional application claims priority under 35 U.S.C. §119(a) on Patent Application No. 2010-266200 filed in JAPAN on Nov. 30, 2010 and on Patent Application No. 2011-043586 filed in JAPAN on Mar. 1, 2011, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

US 2007/0122750 A1 discloses a salt represented by the following formula:

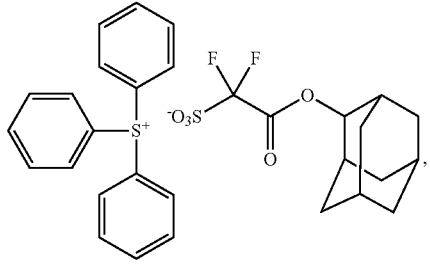

and a photoresist composition containing the same as an acid generator.

SUMMARY OF THE INVENTION

The present invention is to provide a salt for suitable for an acid generator and a photoresist composition comprising the same.

The present invention relates to the followings:

<1> A salt represented by the formula (I):

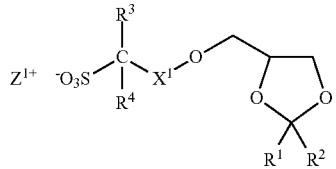

wherein $R^1$ and $R^2$ independently each represent a C1-C6 alkyl group or $R^1$ and $R^2$ are bonded each other to form a C5-C20 aliphatic ring together with the carbon atom to which they are bonded, $R^3$ and $R^4$ independently each represent a fluorine atom or a C1-C6 perfluoroalkyl group, $X^1$ represents a C1-C17 divalent saturated hydrocarbon group in which one or more —$CH_2$— can be replaced by —O— or —CO— and which may be substituted with one or more fluorine atoms, and $Z^{1+}$ represents an organic counter ion;

<2> The salt according to <1>, wherein the C5-C20 aliphatic ring formed by bonding $R^1$ and $R^2$ each other together with the carbon atom to which they are bonded is a cyclohexane ring;

<3> The salt according to <1> or <2>, wherein $X^1$ is *—CO— or a group represented by the following:

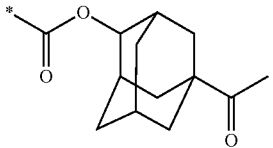 [SMILES: *C(=O)OC1C2CC3CC1CC(C(C)=O)(C3)C2]

wherein * represents a binding position to —$C(R^3)(R^4)$—;

<4> The salt according to any one of <1> to <3>, wherein $Z^+$ is a triarylsulfonium cation;

<5> An acid generator comprising the salt according to any one of <1> to <4>;

<6> A photoresist composition comprising the acid generator according to <5> and a resin having an acid-labile group, being insoluble or poorly soluble in an aqueous alkali solution but becoming soluble in an aqueous alkali solution by the action of an acid;

<7> The photoresist composition according to <6>, which further comprises a basic compound;

<8> A process for producing a photoresist pattern comprising the following steps (1) to (5):
(1) a step of applying the photoresist composition according to <6> or <7> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

First, the salt represented by the formula (I) will be illustrated.

The salt of the present invention is represented by the formula (I):

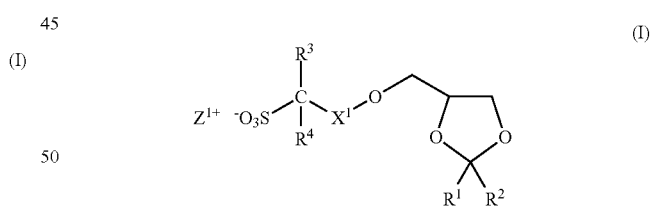

wherein $R^1$ and $R^2$ independently each represent a C1-C6 alkyl group or $R^1$ and $R^2$ are bonded each other to form a C5-C20 aliphatic ring together with the carbon atom to which they are bonded, $R^3$ and $R^4$ independently each represent a fluorine atom or a C1-C6 perfluoroalkyl group, $X^1$ represents a C1-C17 divalent saturated hydrocarbon group in which one or more —$CH_2$— can be replaced by —O— or —CO— and which may be substituted with one or more fluorine atoms, and $Z^{1+}$ represents an organic counter ion (hereinafter, simply referred to as SALT (I)).

Examples of the C1-C6 alkyl group include a methyl group, an ethyl group, a propyl group, an isopropyl group, a butyl group, a sec-butyl group, a tert-butyl group, a pentyl group and a hexyl group.

Examples of the C5-C20 aliphatic ring formed by bonding $R^1$ and $R^2$ each other together with the carbon atom to which they are bonded include a cyclopentane ring, a cyclohexane ring, a cycloheptane ring and an adamantane ring, and a cyclohexane ring is preferable.

Examples of the C1-C6 perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group, and a trifluoromethyl group is preferable. It is preferred that $R^3$ and $R^4$ independently each represent a fluorine atom or a trifluoromethyl group, and it is more preferred that $R^3$ and $R^4$ are fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group; a C2-C17 branched alkanediyl group such as a butane-1,3-diyl group, a 2-methylpropane-1,3-diyl group, a 2-methylpropane-1,2-diyl group, a pentane-1,4-diyl group and a 2-methylbutane-1,4-diyl group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantine-1,5-diyl group and an adamantane-2,6-diyl group; and a group formed by combining two or more groups selected from the group consisting of the above-mentioned groups.

The C1-C17 divalent saturated hydrocarbon group may be substituted with one or more fluorine atoms, and examples of the C1-C17 divalent saturated hydrocarbon group substituted with one or more fluorine atoms include the following.

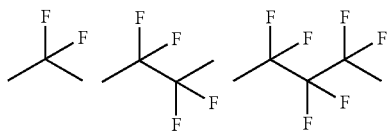

The C1-C17 divalent saturated hydrocarbon group in which one or more —CH$_2$— can be replaced by —O— or —CO—.

When $X^1$ represents a C1-C17 divalent saturated hydrocarbon group in which one or more —CH$_2$— are replaced by —O— or —CO—, examples thereof include the groups represented by the formulae (X1-A), (X1-B), (X1-C), (X1-D) (X1-E) and (X1-F):

(X1-A)

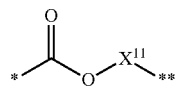

(X1-B)

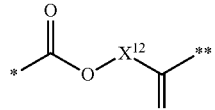

(X1-C)

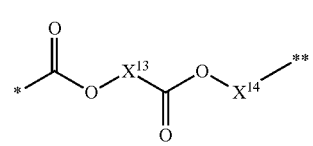

(X1-D)

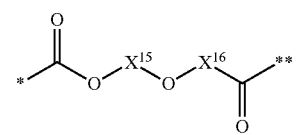

(X1-E)

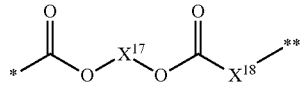

(X1-F)

wherein $X^{11}$ represents a C1-C15 divalent saturated hydrocarbon group, $X^{12}$ represents a C1-C14 divalent saturated hydrocarbon group, $X^{13}$ represents C1-C12 divalent saturated hydrocarbon group, $X^{14}$ represents C1-C12 divalent saturated hydrocarbon group, with the proviso that total carbon number of $X^{13}$ and $X^{14}$ is 1 to 13, $X^{15}$ represents C1-C12 divalent saturated hydrocarbon group, $X^{16}$ represents C1-C12 divalent saturated hydrocarbon group, with the proviso that total carbon number of $X^{15}$ and $X^{16}$ is 1 to 1,3, $X^{17}$ represents C1-C12 divalent saturated hydrocarbon group, $X^{18}$ represents C1-C12 divalent saturated hydrocarbon group, with the proviso that total carbon number of $X^{17}$ and $X^{18}$ is 1 to 13, * represents a binding position to —C($R^3$)($R^4$)— and ** represents a binding position to —O—.

$X^1$ is preferably the group represented by the formula (X1-A) or (X1-B), and more preferably the group represented by the formula (X1-A).

Each of $X^{11}$ to $X^{18}$ is preferably —CH$_2$—, —(CH$_2$)$_2$—, —(CH$_2$)$_4$—, (CH$_2$)$_8$— or —(CH$_2$)$_{12}$—.

Examples of the group represented by the formula (X1-B) include the following.

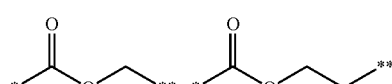

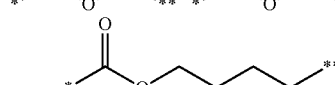

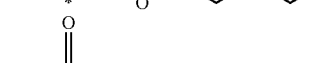

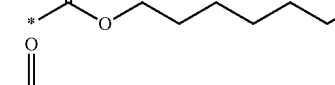

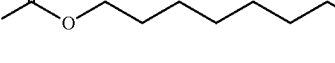

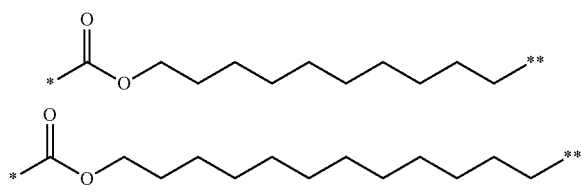
Examples of the group represented by the formula (X1-C) include the following.
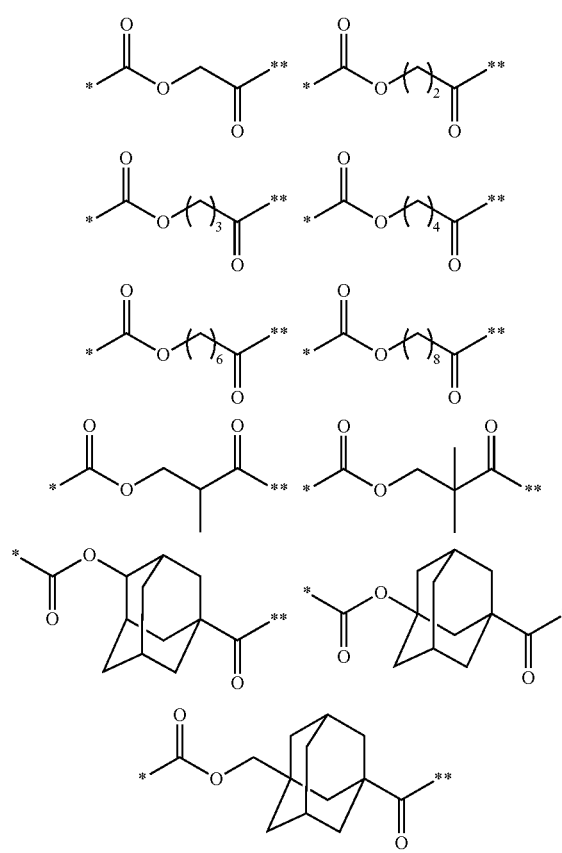
Examples of the group represented by the formula (X1-D) include the following.
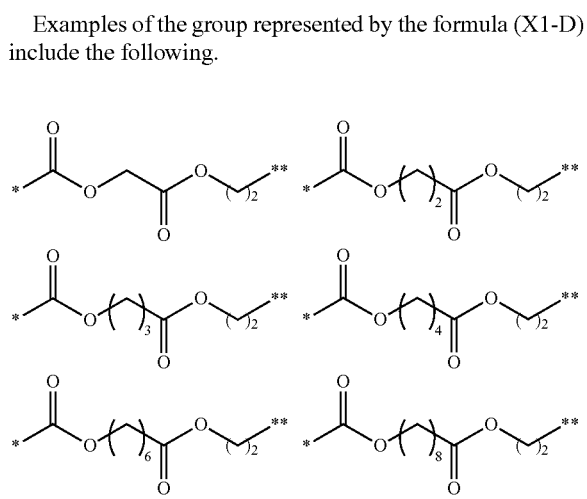
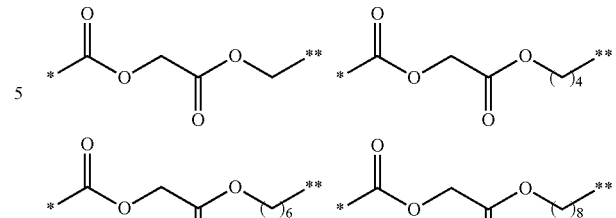
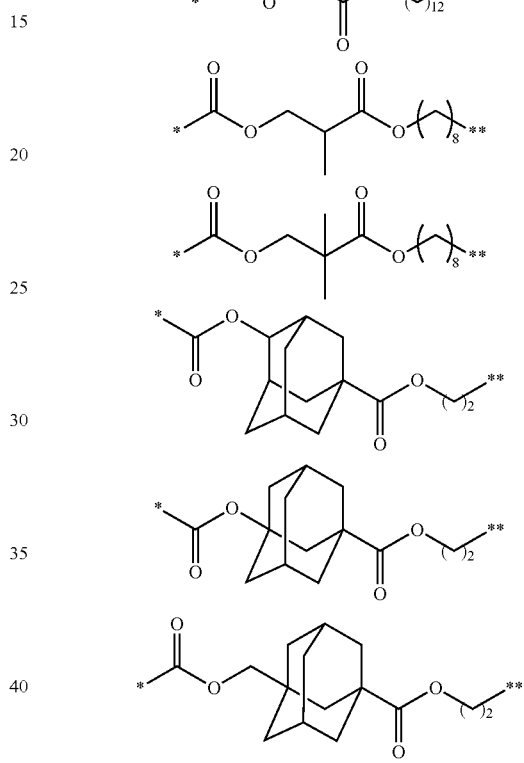
Examples of the group represented by the formula (X1-E) include the following.
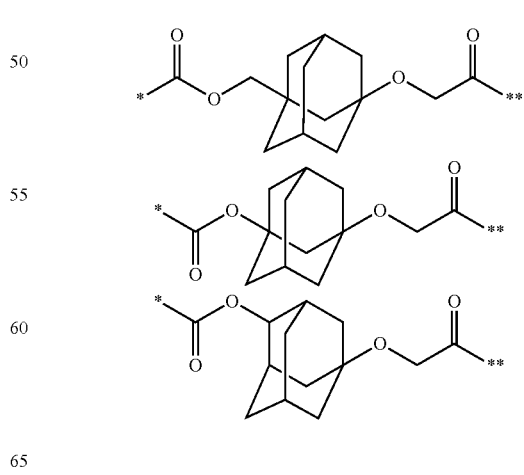
Examples of the group represented by the formula (X1-F) include the following.

Examples of the anion part of SALT (I) include the anions represented by the following formulae (I-a-1) to (I-a-24).

(I-a-12)
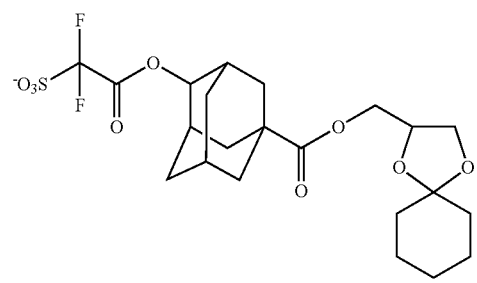
(I-a-18)
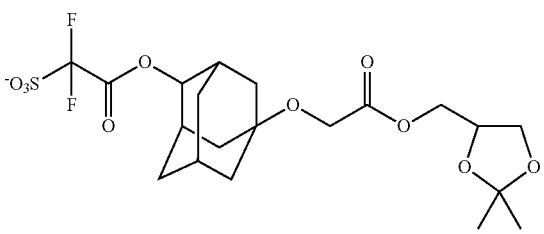
(I-a-13)
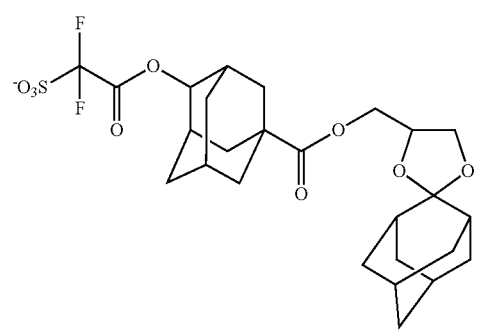
(I-a-19)
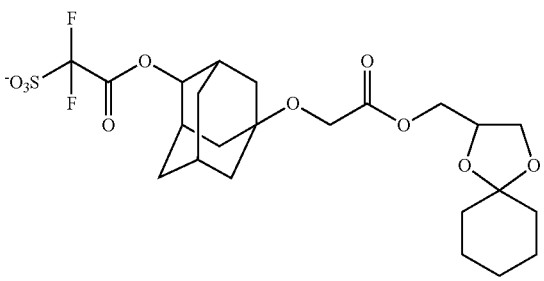
(I-a-14)
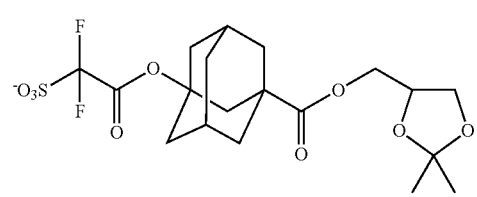
(I-a-20)
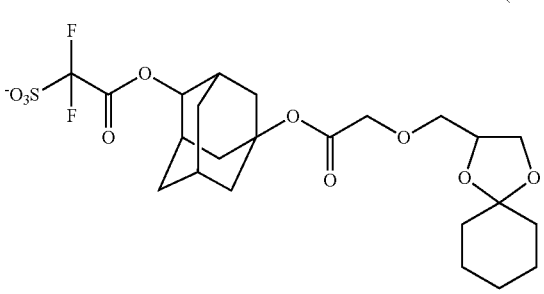
(I-a-15)
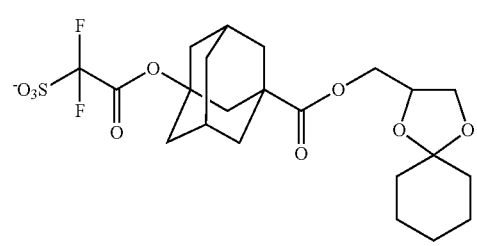
(I-a-21)
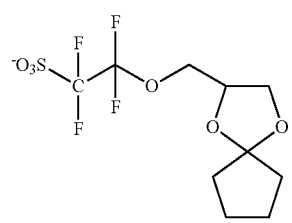
(I-a-16)
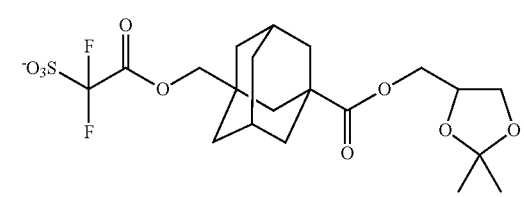
(I-a-22)
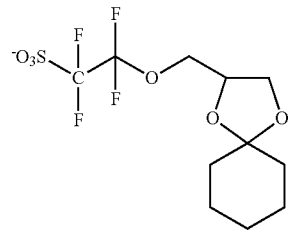
(I-a-17)
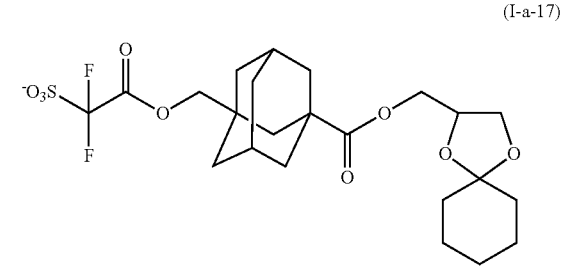
(I-a-23)
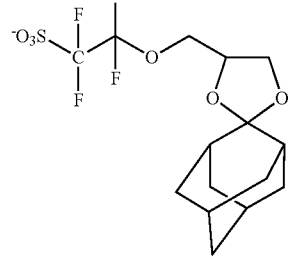

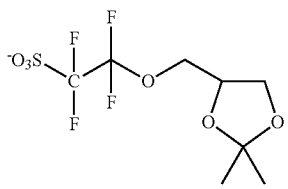

(I-a-24)

Examples of the organic counter ion represented by $Z^{1+}$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable, and a triarylsulfonium cation is especially preferable. "Arylsulfonium cation" means a cation having at least one aryl group.

Preferable examples of the organic counter ion represented by $Z^{1+}$ include the organic cations represented by the formulae (b2-1) to (b2-4):

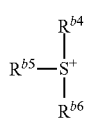

(b2-1)

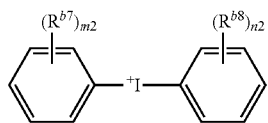

(b2-2)

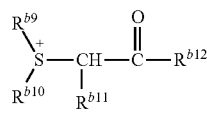

(b2-3)

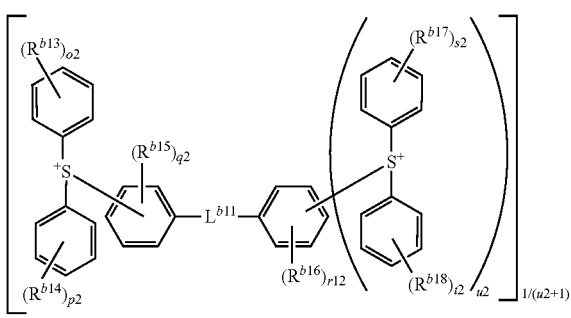

(b2-4)

wherein $R^{b4}$, $R^{b5}$ and $R^{b6}$ independently represent a C1-C30 alkyl group which can have one or more substituents selected from the group consisting of a hydroxyl group, a C1-C12 alkoxy group and a C6-C18 aromatic hydrocarbon group, a C3-C18 alicyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 alkyl group, a C3-C18 alicyclic hydrocarbon group and a C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 alkyl group or a C1-C12 alkoxy group, m2 and n2 independently represents an integer of 0 to 5,
$R^{b9}$ and $R^{b10}$ independently represent a C1-C18 alkyl group or a C3-C18 alicyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and
$R^{b11}$ represents a hydrogen atom, a C1-C18 alkyl group, a C3-C18 alicyclic hydrocarbon group or a C6-C18 aromatic hydrocarbon group, $R^{b12}$ represents a C1-C12 alkyl group, a C3-C18 alicyclic hydrocarbon group or a C6-C18 aromatic hydrocarbon group and the aromatic hydrocarbon group can have one or more substituents selected from the group consisting of a C1-C12 alkyl group, a C1-C12 alkoxy group, a C3-C18 alicyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and
$R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b9}$ to $R^{b11}$ has preferably 1 to 12 carbon atoms. The alicyclic hydrocarbon group represented by $R^{b9}$ to $R^{b11}$ has preferably 4 to 12 carbon atoms.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a 2-ethylhexyl group, a decyl group, a dodecyl group, a hexadecyl group, a pentadecyl group, a heptadecyl group and an octadecyl group, and more preferable examples thereof include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the alicyclic hydrocarbon group represented by $R^{b4}$ to $R^{b6}$ include a cyclopropyl group, a cyclobutyl group, a cyclopentyl group, a cyclohexyl group, a cycloheptyl group, a cyclodecyl group, an adamantyl group, a 2-alkyladamantan-2-yl group, a 1-(adamantan-1-yl)alkan-1-yl group and an isobornyl group, and more preferable examples thereof include a cyclopropyl group, a cyclobutyl group, a cyclopentyl group, a cyclohexyl group, a cycloheptyl group, a cyclodecyl group, a 2-alkyladamantan-2-yl group, a 1-(adamantan-1-yl)alkan-1-yl group, and an isobornyl group.

Preferable examples of the aromatic group include represented by $R^{b4}$ to $R^{b6}$ a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propionyl group, a butyryl group, isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Examples of the aliphatic hydrocarbon group having an aromatic hydrocarbon group include a benzyl group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b1}$ and $R^{b12}$ include a methylene group, an ethylene group, a trimethylene group, a tetramethylene group and a pentamethylene group and examples of the ring group include the followings.

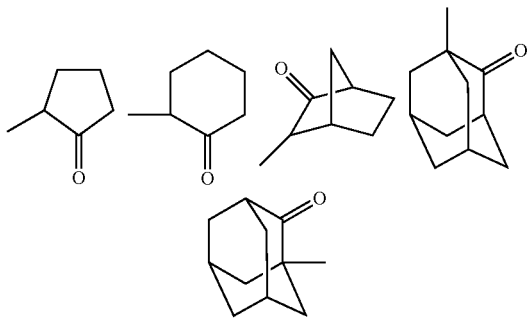

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation and a trytolysulfonium cation are especially preferable.

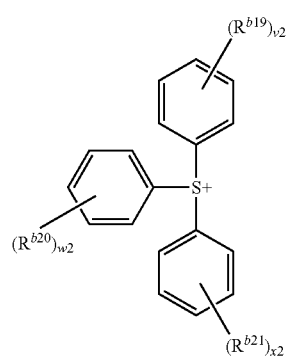

(b2-1-1)

wherein $R^{b19}$, $R^{b20}$ and $R^{b21}$ are independently in each occurrence a halogen atom (preferably a fluorine atom), a hydroxyl group, a C1-C18 alkyl group, a C3-C18 alicyclic hydrocarbon group or a C1-C12 alkoxy group, and one or more hydrogen atoms of the alkyl group can be replaced by a hydroxyl group, a C1-C12 alkoxy group or a C6-C18 aromatic hydrocarbon group, and one or more hydrogen atoms of the alicyclic hydrocarbon group can be replaced by a halogen atom, a glycidyloxy group or a C2-C4 acyl group, and $R^{b19}$ and $R^{b20}$, $R^{b19}$ and $R^{b21}$ or $R^{b20}$ and $R^{b21}$ can be bonded each other to form a single bond, —O— or a C1-C4 aliphatic divalent hydrocarbon group which forms a sulfur containing ring together with $S^+$ and v2, w2 and x2 independently each represent an integer of 0 to 5.

The alkyl group has preferably 1 to 12 carbon atoms, and the alicyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the organic counter ion include those described in JP 2010-204646 A.

Preferable examples of the organic counter ion include the following.

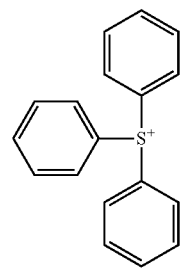

(I-c-1)

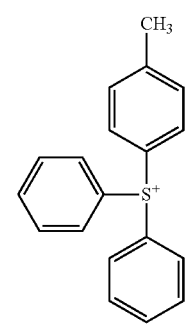

(I-c-2)

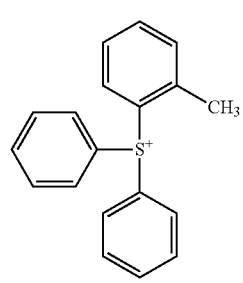

(I-c-3)

(I-c-4)
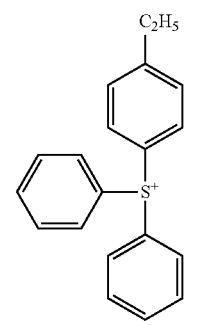
(I-c-5)
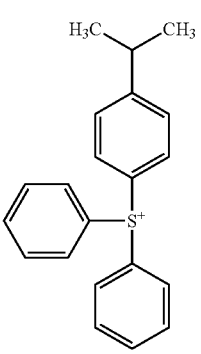
(I-c-6)
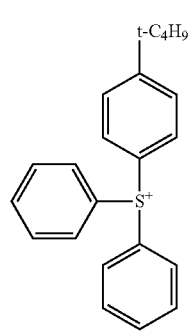
(I-c-7)
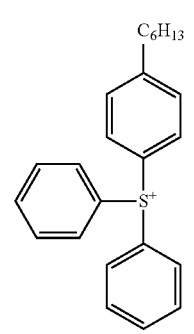
(I-c-8)
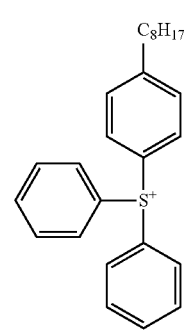
(I-c-9)
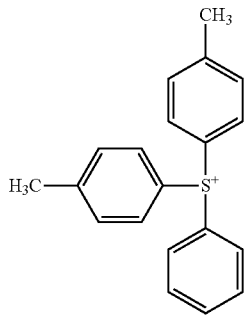
(I-c-10)
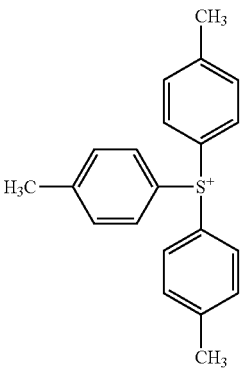
(I-c-11)
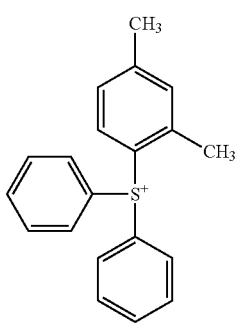
(I-c-12)
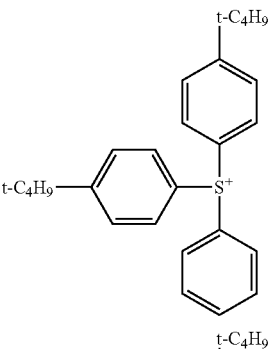
(I-c-13)
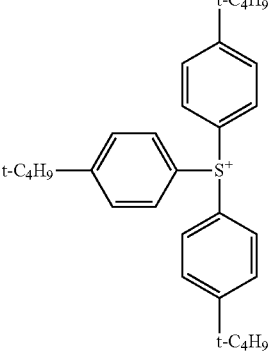

(I-c-14)
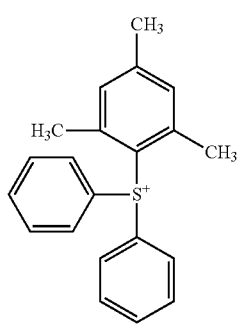
(I-c-15)
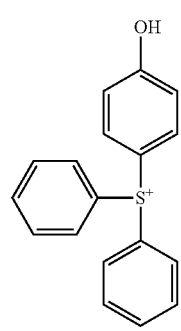
(I-c-16)
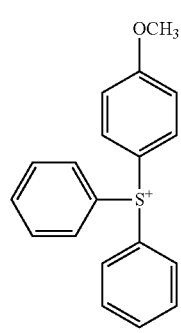
(I-c-17)
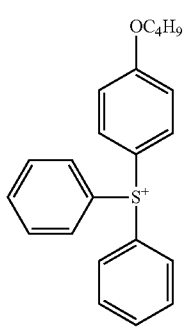
(I-c-18)
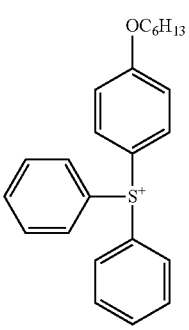
(b2-c-18)
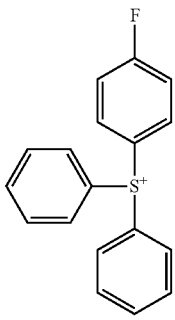
(b2-c-19)
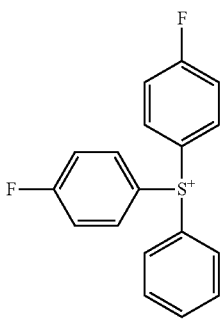
(b2-c-20)
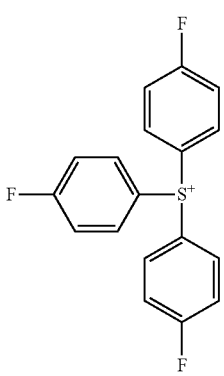
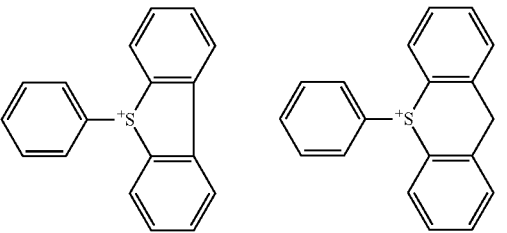
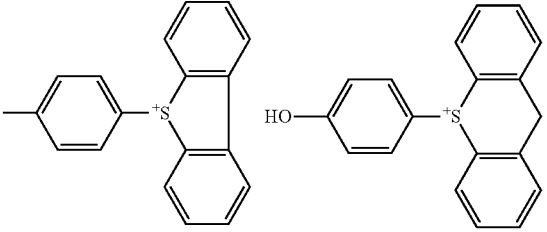

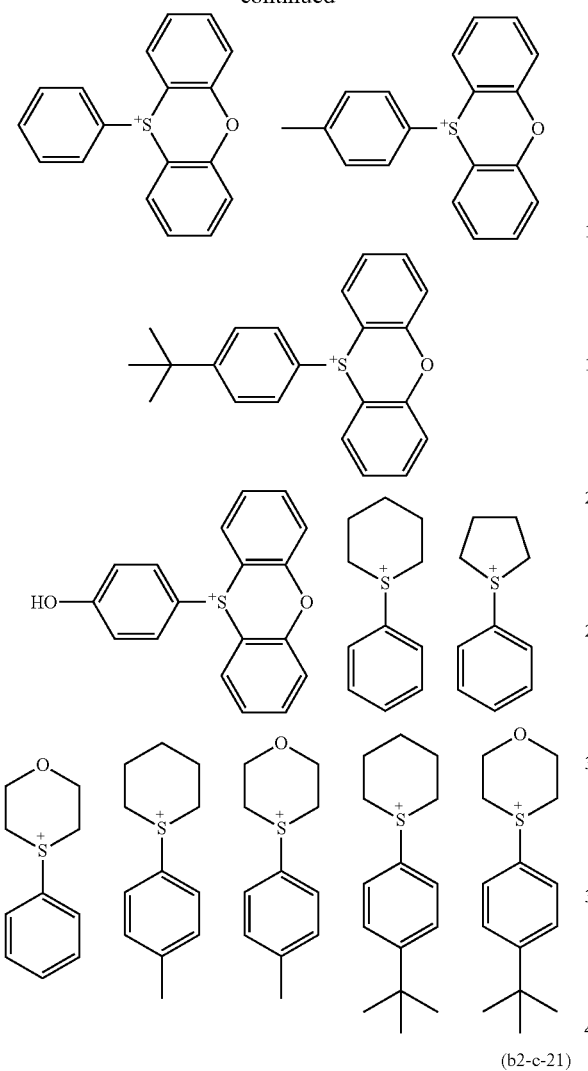
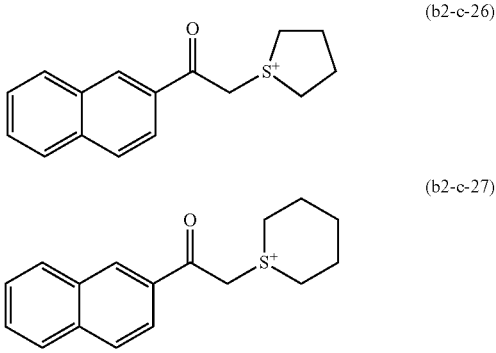

Examples of SALT (I) include a salt wherein the anion is any one of the above-mentioned anions and the cation is any one of organic counter ions. Preferable examples of SALT (I) include the following salts described in Tables 1 to 7.

TABLE 1

| SALT (I) | Anion | Counter Ion |
|---|---|---|
| (I-1) | (I-a-2) | (I-c-1) |
| (I-2) | (I-a-1) | (I-c-1) |
| (I-3) | (I-a-3) | (I-c-1) |
| (I-4) | (I-a-4) | (I-c-1) |
| (I-5) | (I-a-5) | (I-c-1) |
| (I-6) | (I-a-6) | (I-c-1) |
| (I-7) | (I-a-7) | (I-c-1) |
| (I-8) | (I-a-8) | (I-c-1) |
| (I-9) | (I-a-9) | (I-c-1) |
| (I-10) | (I-a-10) | (I-c-1) |

TABLE 2

| SALT (I) | Anion | Counter Ion |
|---|---|---|
| (I-11) | (I-a-1) | (I-c-10) |
| (I-12) | (I-a-2) | (I-c-10) |
| (I-13) | (I-a-3) | (I-c-10) |
| (I-14) | (I-a-4) | (I-c-10) |
| (I-15) | (I-a-5) | (I-c-10) |
| (I-16) | (I-a-6) | (I-c-10) |
| (I-17) | (I-a-7) | (I-c-10) |
| (I-18) | (I-a-8) | (I-c-10) |
| (I-19) | (I-a-9) | (I-c-10) |
| (I-20) | (I-a-10) | (I-c-10) |
| (I-21) | (I-a-1) | (I-c-21) |
| (I-22) | (I-a-2) | (I-c-21) |
| (I-23) | (I-a-3) | (I-c-21) |
| (I-24) | (I-a-4) | (I-c-21) |
| (I-25) | (I-a-5) | (I-c-21) |
| (I-26) | (I-a-6) | (I-c-21) |
| (I-27) | (I-a-7) | (I-c-21) |
| (I-28) | (I-a-8) | (I-c-21) |
| (I-29) | (I-a-9) | (I-c-21) |
| (I-30) | (I-a-10) | (I-c-21) |
| (I-31) | (I-a-1) | (I-c-24) |
| (I-32) | (I-a-2) | (I-c-24) |
| (I-33) | (I-a-3) | (I-c-24) |
| (I-34) | (I-a-4) | (I-c-24) |
| (I-35) | (I-a-5) | (I-c-24) |
| (I-36) | (I-a-6) | (I-c-24) |
| (I-37) | (I-a-7) | (I-c-24) |
| (I-38) | (I-a-8) | (I-c-24) |
| (I-39) | (I-a-9) | (I-c-24) |
| (I-40) | (I-a-10) | (I-c-24) |

TABLE 3

| SALT (I) | Anion | Counter Ion |
|---|---|---|
| (I-41) | (I-a-2) | (I-c-2) |
| (I-42) | (I-a-6) | (I-c-2) |
| (I-43) | (I-a-9) | (I-c-2) |
| (I-44) | (I-a-10) | (I-c-2) |
| (I-45) | (I-a-2) | (I-c-6) |
| (I-46) | (I-a-6) | (I-c-6) |
| (I-47) | (I-a-9) | (I-c-6) |
| (I-48) | (I-a-10) | (I-c-6) |
| (I-49) | (I-a-2) | (I-c-15) |
| (I-50) | (I-a-6) | (I-c-15) |
| (I-51) | (I-a-9) | (I-c-15) |
| (I-52) | (I-a-10) | (I-c-15) |
| (I-53) | (I-a-2) | (I-c-23) |
| (I-54) | (I-a-6) | (I-c-23) |
| (I-55) | (I-a-9) | (I-c-23) |
| (I-56) | (I-a-10) | (I-c-23) |

TABLE 4

| SALT (I) | Anion | Counter Ion |
|---|---|---|
| (I-57) | (I-a-11) | (I-c-1) |
| (I-58) | (I-a-12) | (I-c-1) |
| (I-59) | (I-a-13) | (I-c-1) |
| (I-60) | (I-a-14) | (I-c-1) |
| (I-61) | (I-a-15) | (I-c-1) |
| (I-62) | (I-a-16) | (I-c-1) |
| (I-63) | (I-a-17) | (I-c-1) |
| (I-64) | (I-a-18) | (I-c-1) |
| (I-65) | (I-a-19) | (I-c-1) |
| (I-66) | (I-a-20) | (I-c-1) |

TABLE 5

| SALT (I) | Anion | Counter Ion |
|---|---|---|
| (I-67) | (I-a-11) | (I-c-10) |
| (I-68) | (I-a-12) | (I-c-10) |
| (I-69) | (I-a-13) | (I-c-10) |
| (I-70) | (I-a-14) | (I-c-10) |
| (I-71) | (I-a-15) | (I-c-10) |
| (I-72) | (I-a-16) | (I-c-10) |
| (I-73) | (I-a-17) | (I-c-10) |
| (I-74) | (I-a-18) | (I-c-10) |
| (I-75) | (I-a-19) | (I-c-10) |
| (I-76) | (I-a-20) | (I-c-10) |
| (I-77) | (I-a-11) | (I-c-21) |
| (I-78) | (I-a-12) | (I-c-21) |
| (I-79) | (I-a-13) | (I-c-21) |
| (I-80) | (I-a-14) | (I-c-21) |
| (I-81) | (I-a-15) | (I-c-21) |
| (I-82) | (I-a-16) | (I-c-21) |
| (I-83) | (I-a-17) | (I-c-21) |
| (I-84) | (I-a-18) | (I-c-21) |
| (I-85) | (I-a-19) | (I-c-21) |
| (I-86) | (I-a-20) | (I-c-21) |
| (I-87) | (I-a-11) | (I-c-24) |
| (I-88) | (I-a-12) | (I-c-24) |
| (I-89) | (I-a-13) | (I-c-24) |
| (I-90) | (I-a-14) | (I-c-24) |
| (I-91) | (I-a-15) | (I-c-24) |
| (I-92) | (I-a-16) | (I-c-24) |
| (I-93) | (I-a-17) | (I-c-24) |
| (I-94) | (I-a-18) | (I-c-24) |
| (I-95) | (I-a-19) | (I-c-24) |
| (I-96) | (I-a-20) | (I-c-24) |

TABLE 6

| SALT (I) | Anion | Counter Ion |
|---|---|---|
| (I-97) | (I-a-11) | (I-c-2) |
| (I-98) | (I-a-12) | (I-c-2) |
| (I-99) | (I-a-13) | (I-c-2) |
| (I-100) | (I-a-18) | (I-c-2) |
| (I-101) | (I-a-19) | (I-c-2) |
| (I-102) | (I-a-20) | (I-c-2) |
| (I-103) | (I-a-11) | (I-c-6) |
| (I-104) | (I-a-12) | (I-c-6) |
| (I-105) | (I-a-13) | (I-c-6) |
| (I-106) | (I-a-18) | (I-c-6) |
| (I-107) | (I-a-19) | (I-c-6) |
| (I-108) | (I-a-20) | (I-c-6) |
| (I-109) | (I-a-11) | (I-c-15) |
| (I-110) | (I-a-12) | (I-c-15) |
| (I-111) | (I-a-13) | (I-c-15) |
| (I-112) | (I-a-18) | (I-c-15) |
| (I-113) | (I-a-19) | (I-c-15) |
| (I-114) | (I-a-20) | (I-c-15) |
| (I-115) | (I-a-11) | (I-c-23) |
| (I-116) | (I-a-12) | (I-c-23) |
| (I-117) | (I-a-13) | (I-c-23) |
| (I-118) | (I-a-18) | (I-c-23) |
| (I-119) | (I-a-19) | (I-c-23) |
| (I-120) | (I-a-20) | (I-c-23) |
| (I-121) | (I-a-21) | (I-c-1) |
| (I-122) | (I-a-22) | (I-c-1) |

TABLE 7

| SALT (I) | Anion | Counter Ion |
|---|---|---|
| (I-123) | (I-a-23) | (I-c-1) |
| (I-124) | (I-a-24) | (I-c-1) |
| (I-125) | (I-a-21) | (I-c-10) |
| (I-126) | (I-a-22) | (I-c-10) |
| (I-127) | (I-a-23) | (I-c-10) |
| (I-128) | (I-a-24) | (I-c-10) |
| (I-129) | (I-a-21) | (I-c-21) |
| (I-130) | (I-a-22) | (I-c-21) |
| (I-131) | (I-a-23) | (I-c-21) |
| (I-132) | (I-a-24) | (I-c-21) |
| (I-133) | (I-a-21) | (I-c-24) |
| (I-134) | (I-a-22) | (I-c-24) |
| (I-135) | (I-a-23) | (I-c-24) |
| (I-136) | (I-a-24) | (I-c-24) |
| (I-137) | (I-a-21) | (I-c-2) |
| (I-138) | (I-a-22) | (I-c-2) |
| (I-139) | (I-a-23) | (I-c-2) |
| (I-140) | (I-a-24) | (I-c-2) |
| (I-141) | (I-a-21) | (I-c-6) |
| (I-142) | (I-a-22) | (I-c-6) |
| (I-143) | (I-a-23) | (I-c-6) |
| (I-144) | (I-a-24) | (I-c-6) |
| (I-145) | (I-a-21) | (I-c-15) |
| (I-146) | (I-a-22) | (I-c-15) |
| (I-147) | (I-a-23) | (I-c-15) |
| (I-148) | (I-a-24) | (I-c-15) |
| (I-149) | (I-a-21) | (I-c-23) |
| (I-150) | (I-a-22) | (I-c-23) |
| (I-151) | (I-a-23) | (I-c-23) |
| (I-152) | (I-a-24) | (I-c-23) |

Among them, preferred are the following.
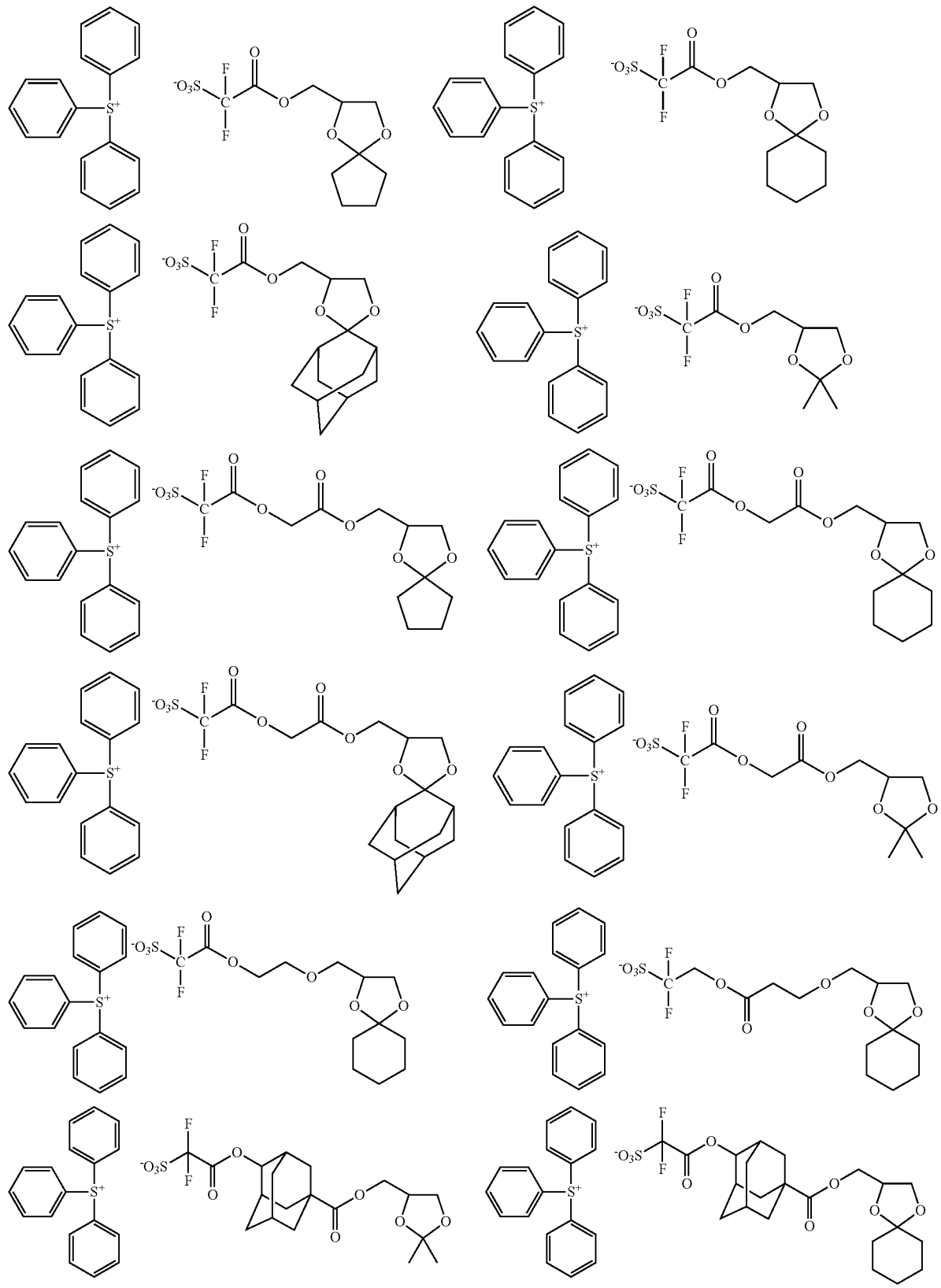

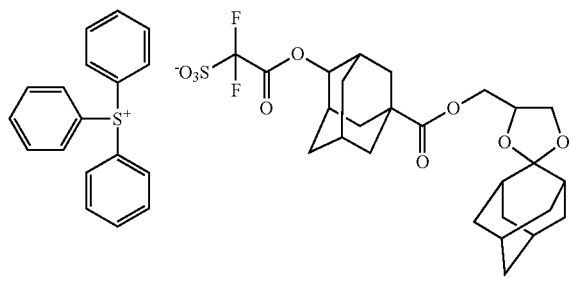
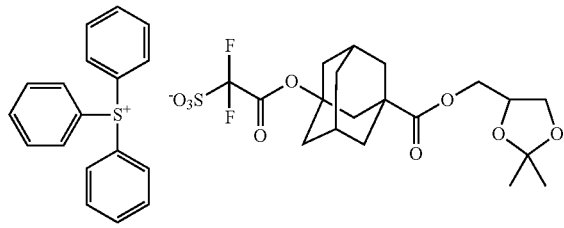
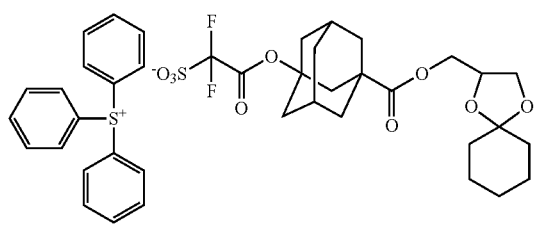
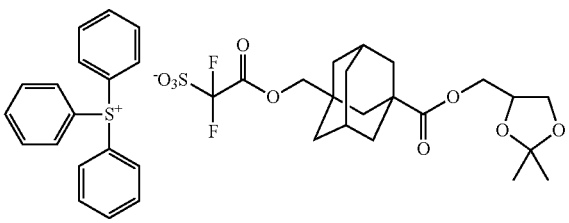
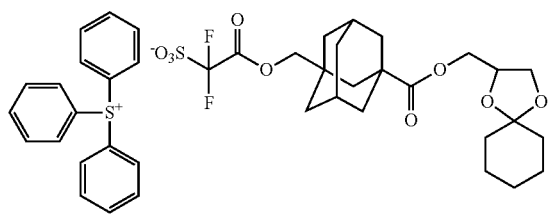
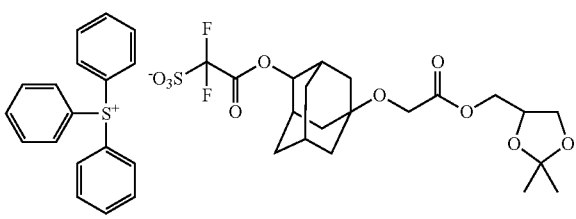
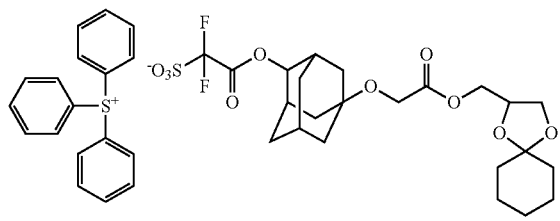
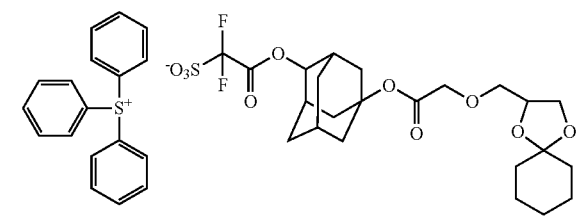
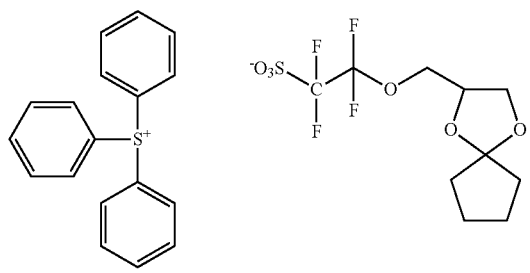
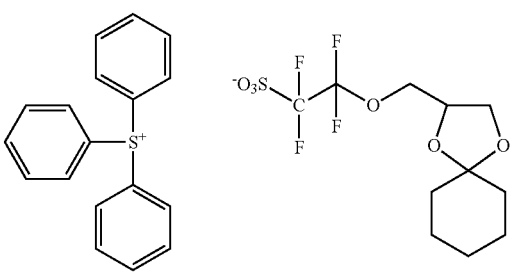
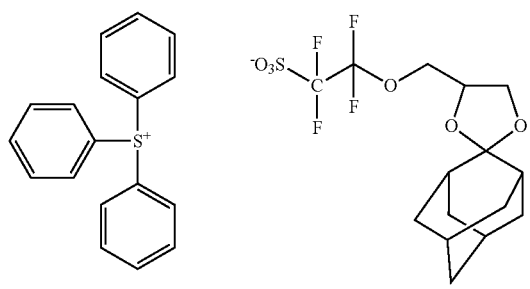
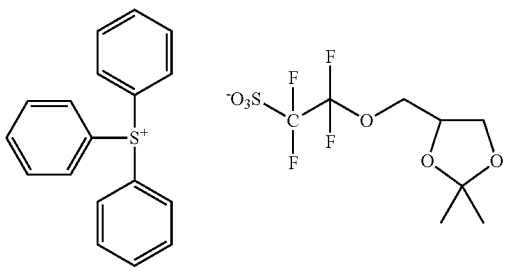

-continued
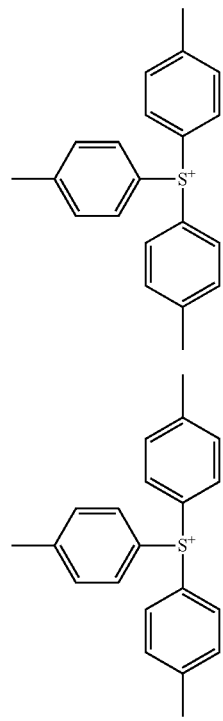 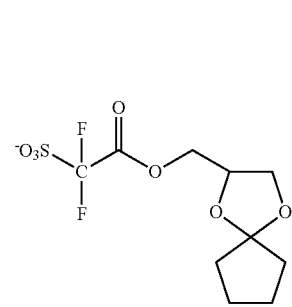 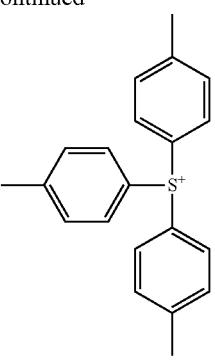 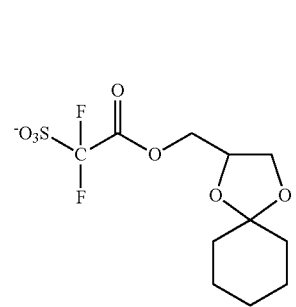
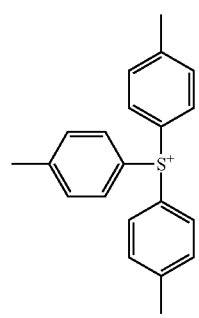 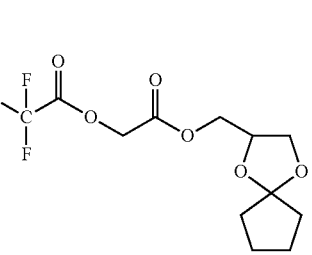 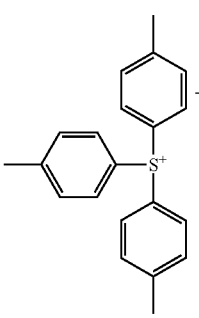 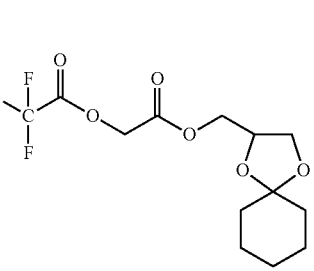
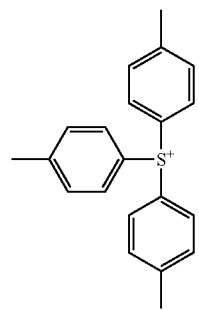 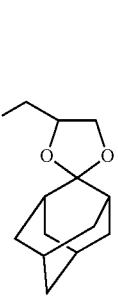 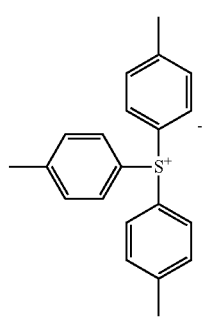 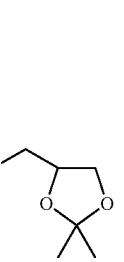
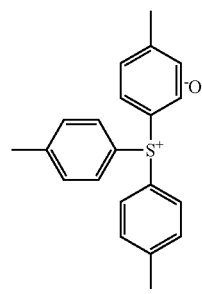 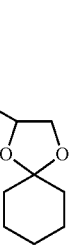 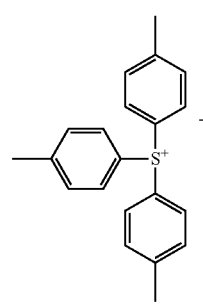 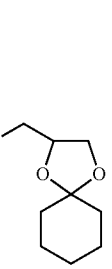

-continued
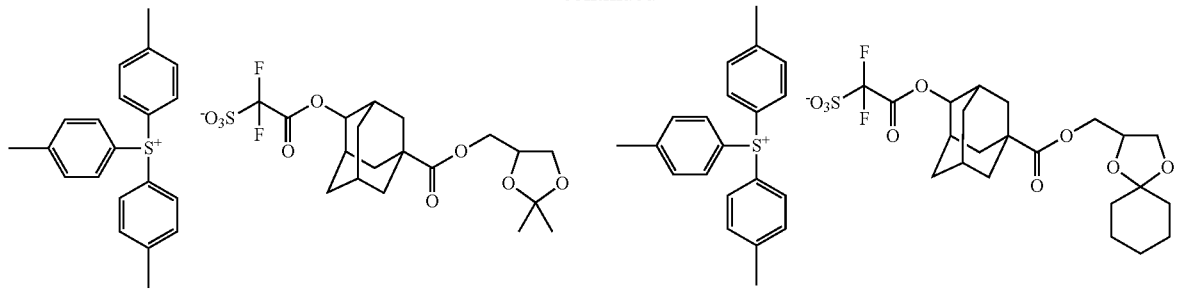
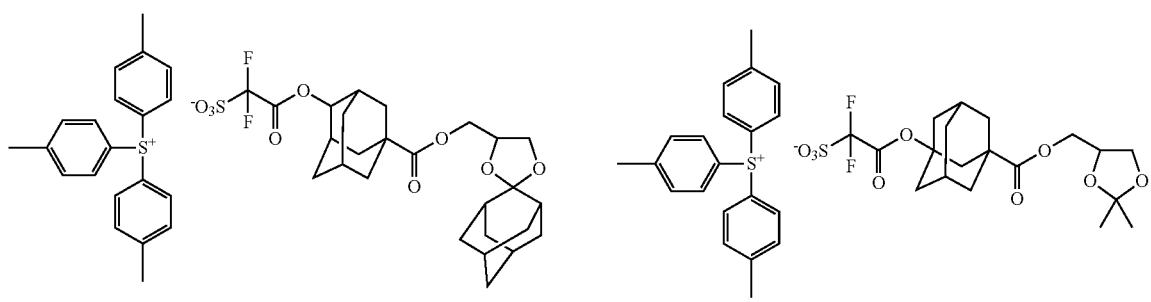
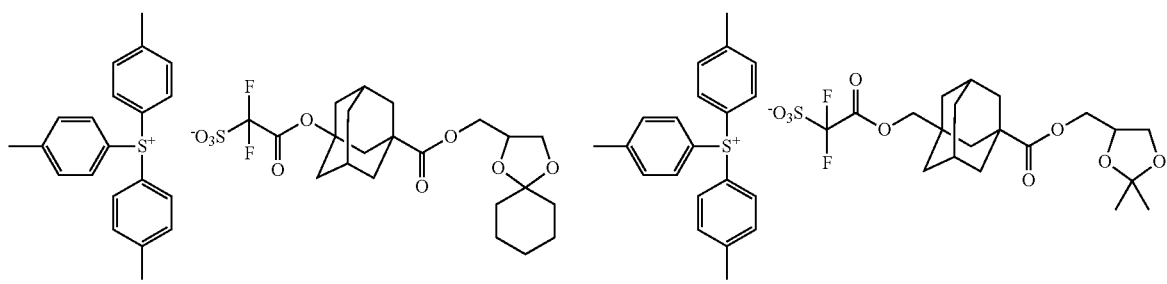
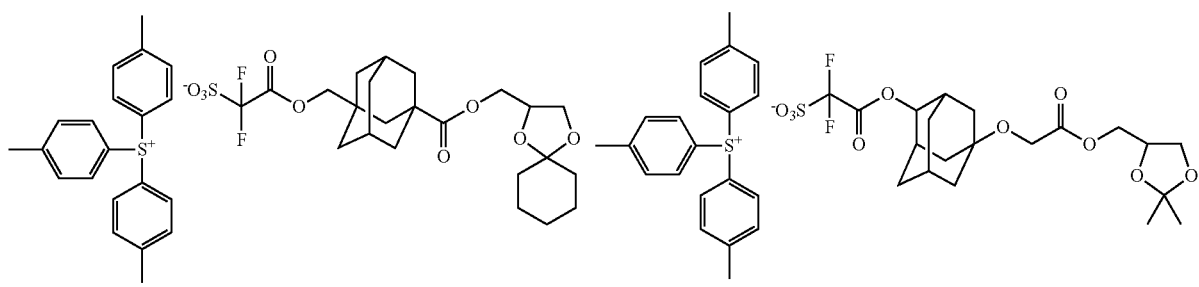
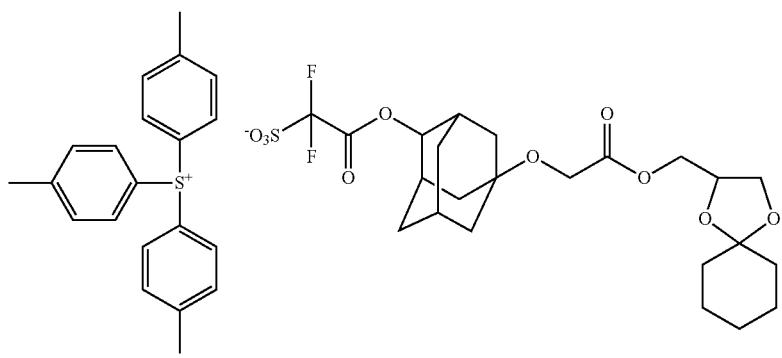

-continued
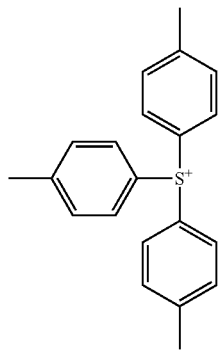 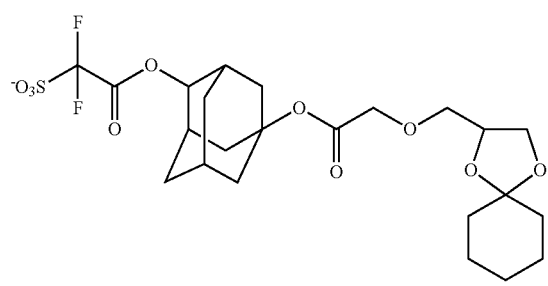
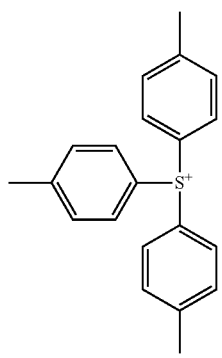 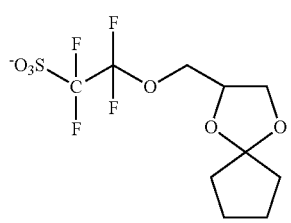 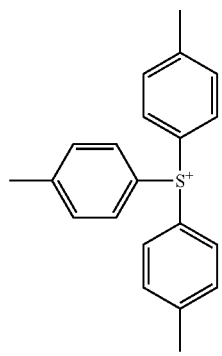 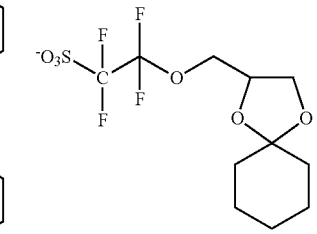
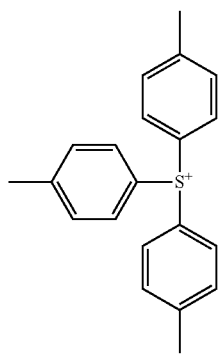 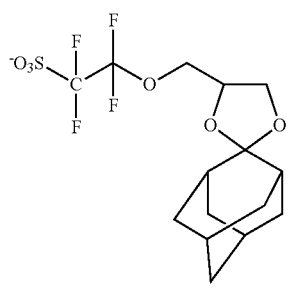 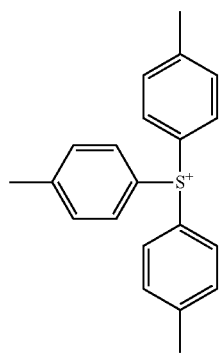 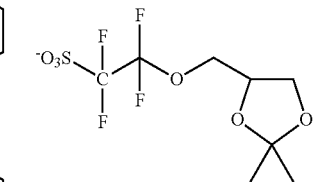
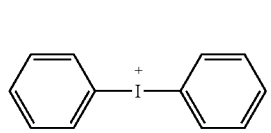 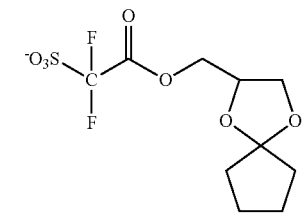 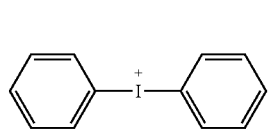 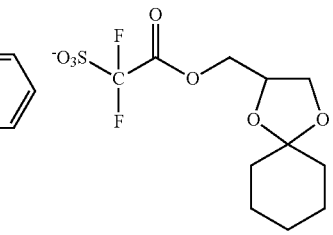
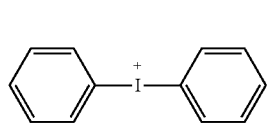 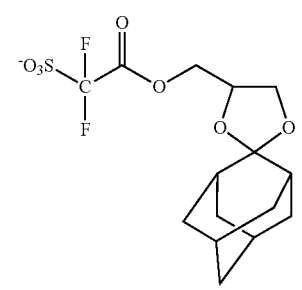 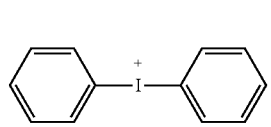 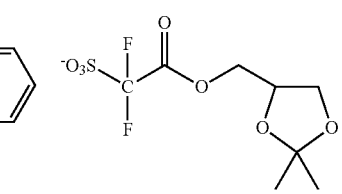

-continued
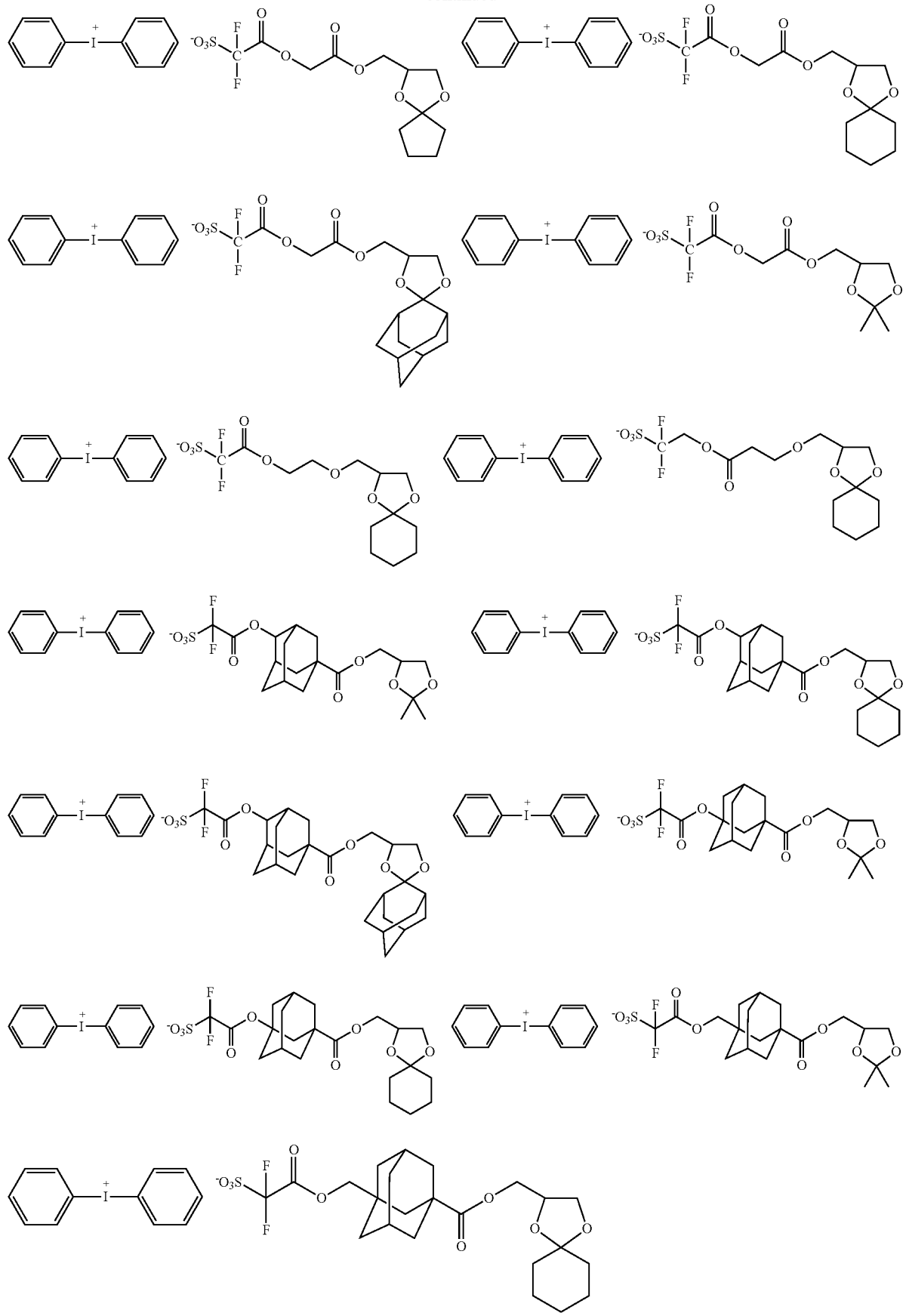

-continued
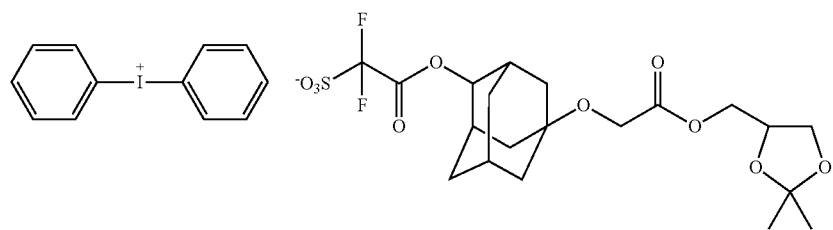
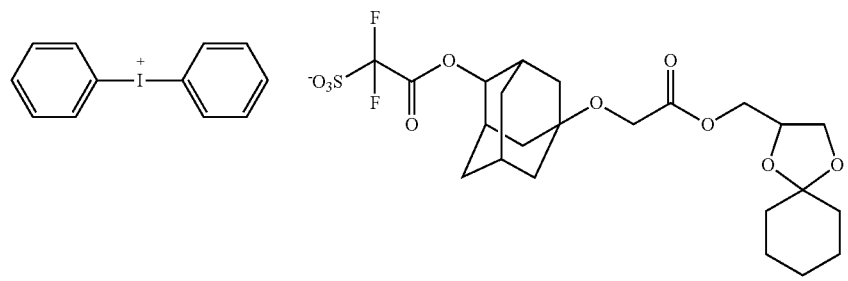
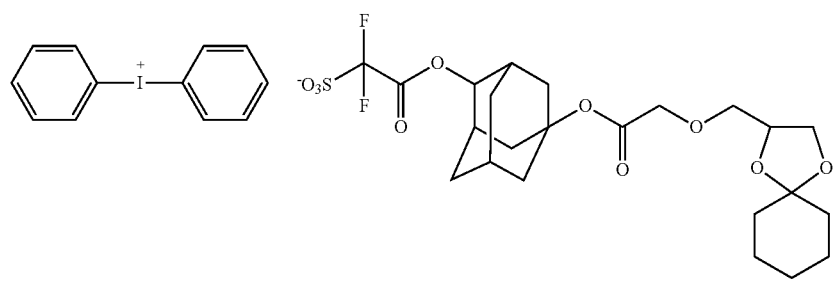
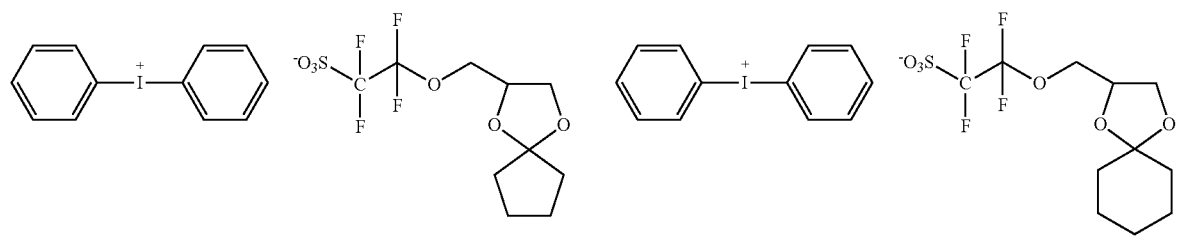
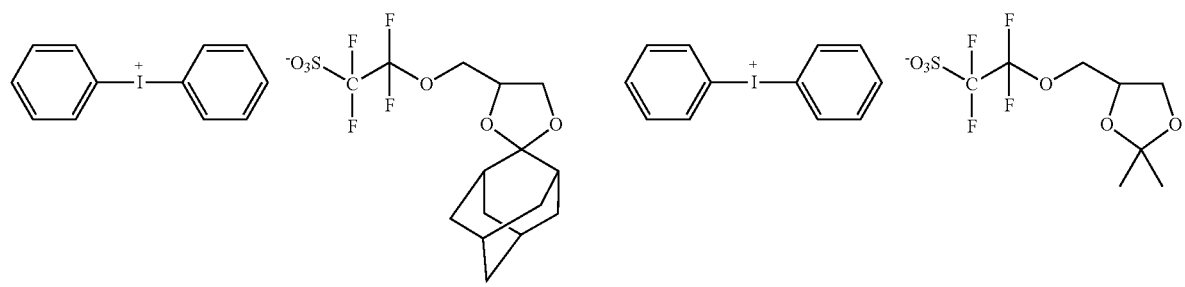
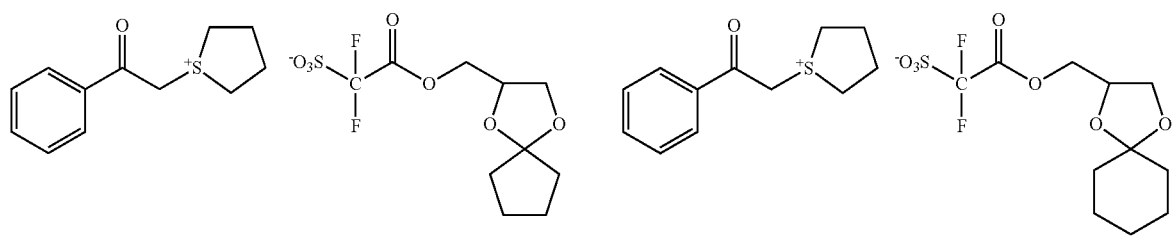

-continued
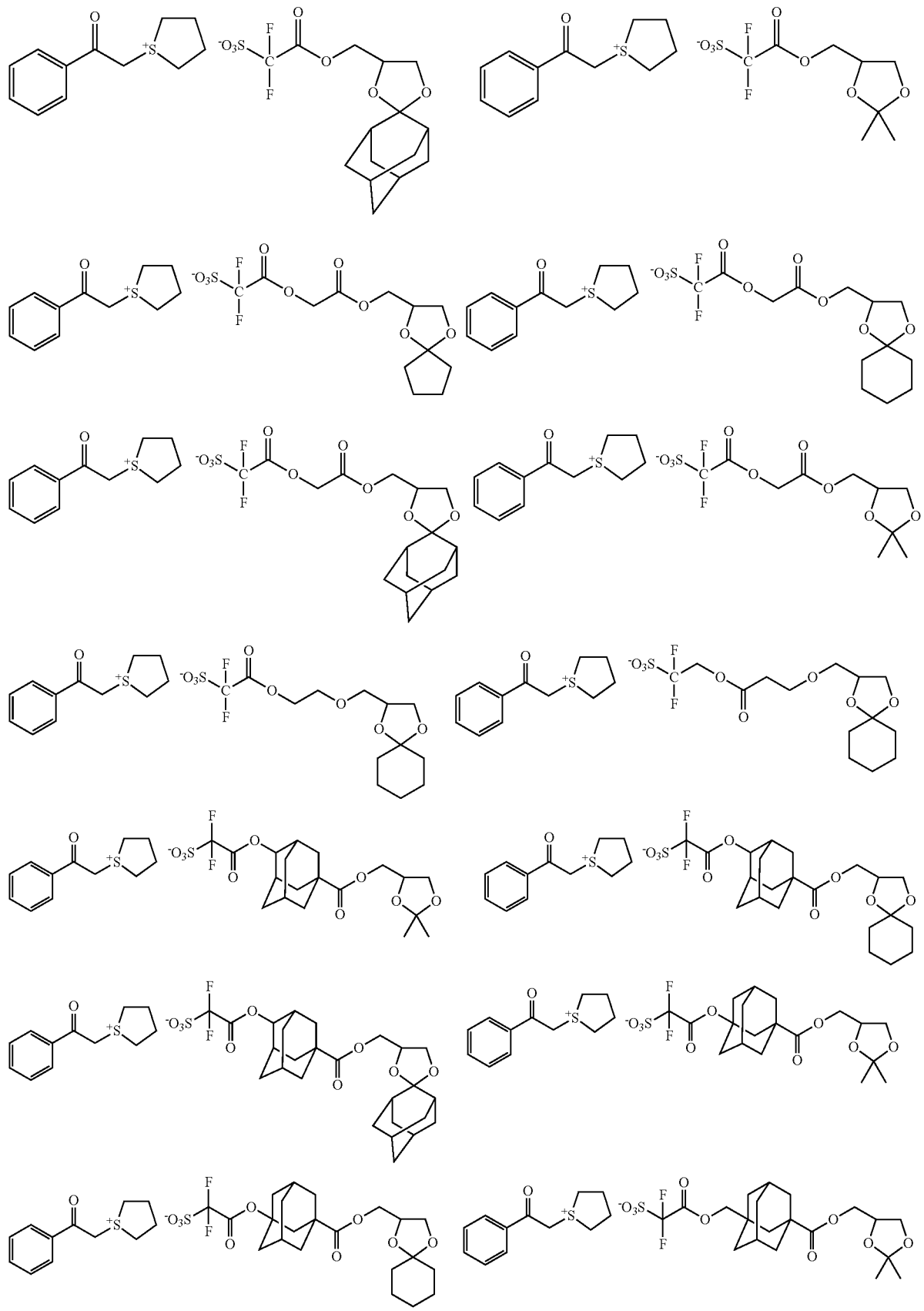

-continued
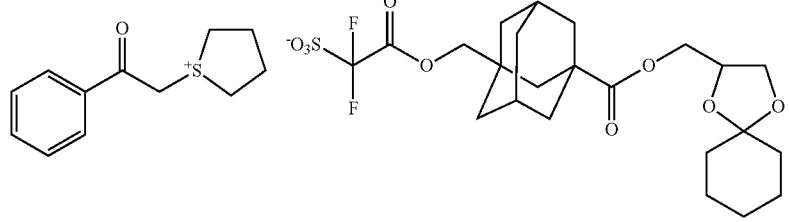
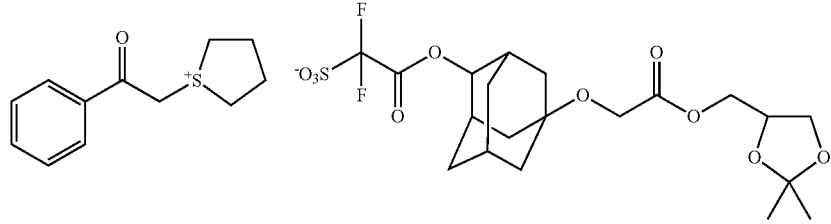
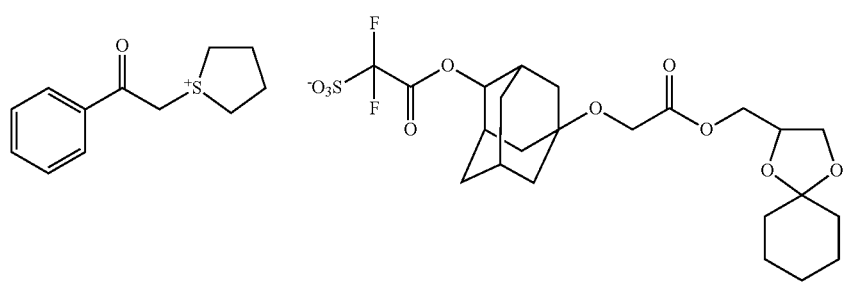
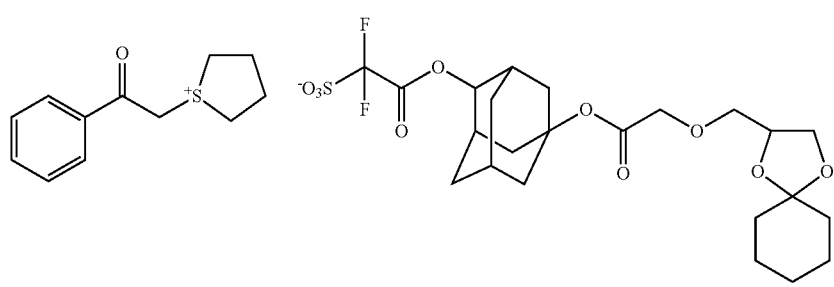
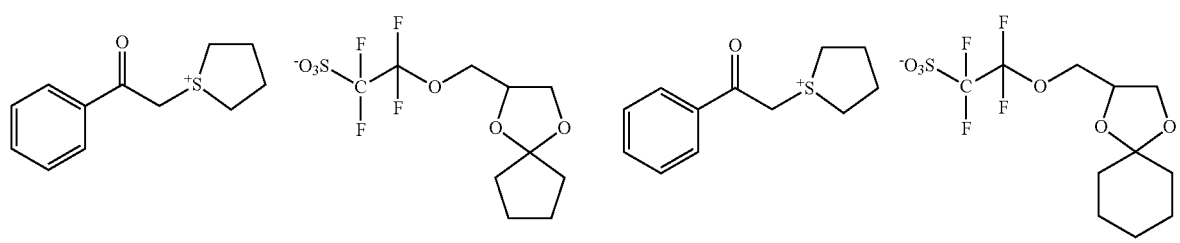
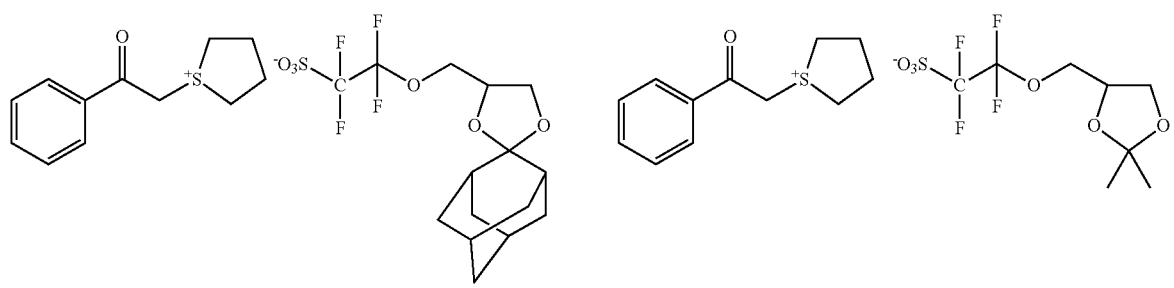

The process for producing SALT (I) will be illustrated.
For example, a salt represented by the formula (b1):

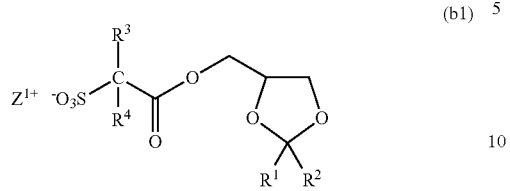

wherein $R^1$, $R^2$, $R^3$, $R^4$ and $Z^{1+}$ are the same as defined above, can be produced by the following process.

The compound represented by the formula (b1-c) can be produced by reacting a salt represented by the formula (b1-a) with a compound represented by the formula (b1-b).

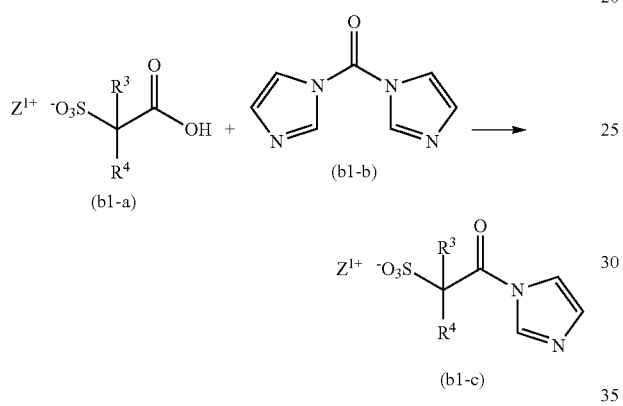

wherein $R^3$, $R^4$ and $Z^{1+}$ are the same as defined above.

The salt represented by the formula (b1-a) can be produced, for example, according to the method described in JP 2008-13551 A.

The salt represented by the formula (b1) can be produced by reacting the salt represented by the formula (b1-c) with a compound represented by the formula (b1-d) in a solvent such as acetonitrile.

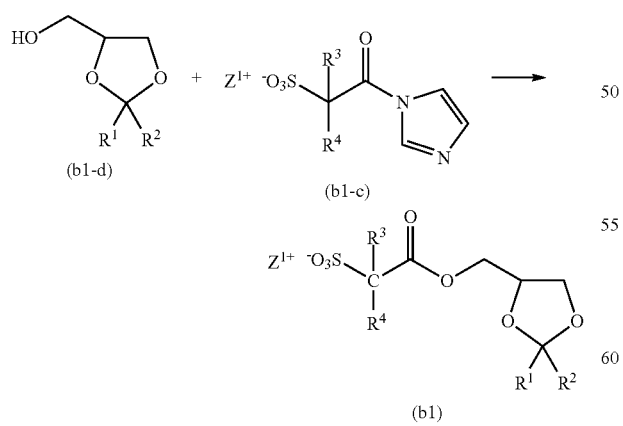

wherein $R^1$, $R^2$, $R^3$, $R^4$ and $Z^{1+}$ are the same as defined above,

Examples of the compound represented by the formula (b1-d) include the following.

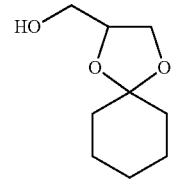

A salt represented by the formula (b2):

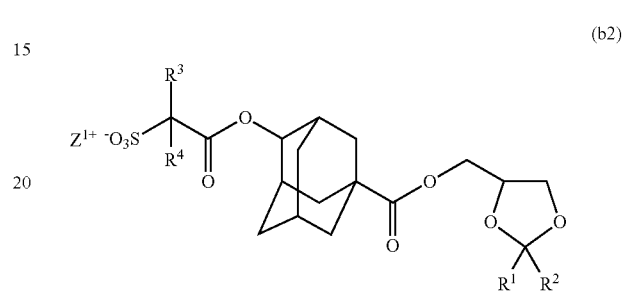

wherein $R^1$, $R^2$, $R^3$, $R^4$ and $Z^{1+}$ are the same as defined above, can be produced by the following process.

The compound represented by the formula (b2-c) can be produced by reacting a compound represented by the formula (b2-a) with a compound represented by the formula (b2-b) in a solvent such as chloroform. The compound represented by the formula (b2-e) can be produced by reacting the compound represented by the formula (b2-c) with a compound represented by the formula (b2-d) in a solvent such as chloroform.

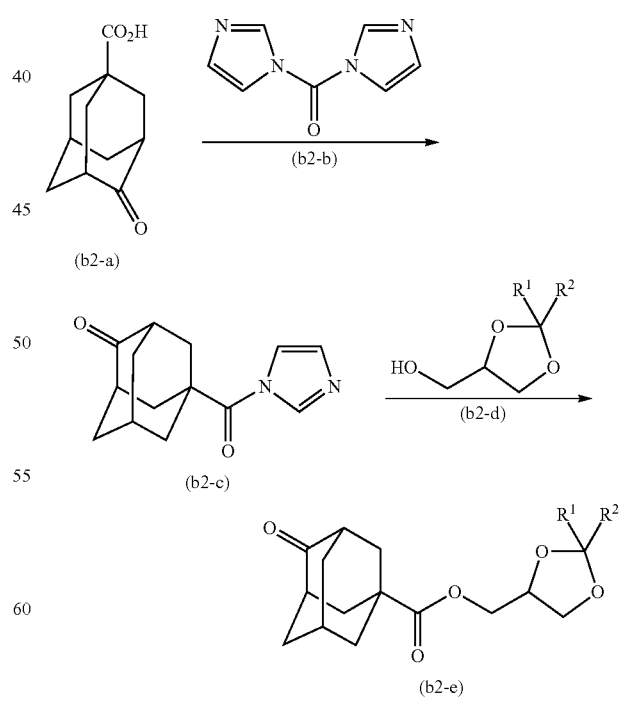

Examples of the compound represented by the formula (b2-d) include the following.

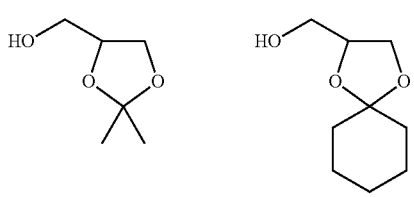

The compound represented by the formula (b2-f) can be produced by reacting the compound represented by the formula (b2-e) with a reducing agent such as sodium borohydride in a solvent such as acetonitrile.

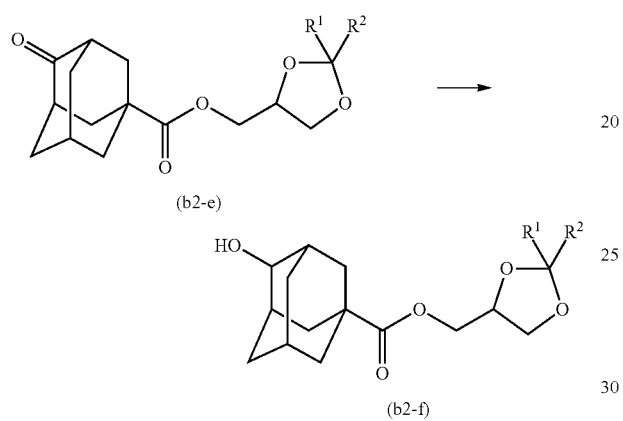

The salt represented by the formula (b2-h) can be produced by reacting a salt represented by the formula (b2-g) with a compound represented by the formula (b2-b). The salt represented by the formula (b1-g) can be produced, for example, according to the method described in JP 2008-13551 A.

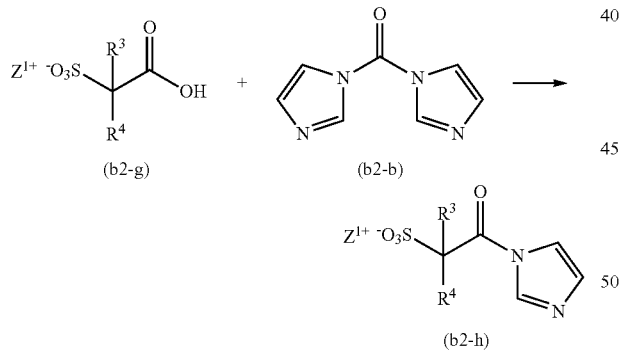

The salt represented by the formula (b2) can be produced by reacting the salt represented by the formula (b2-h) with the compound represented by the formula (b2-f) in a solvent such as acetonitrile.

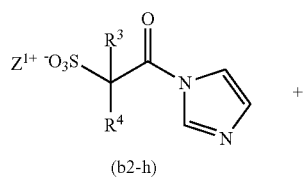

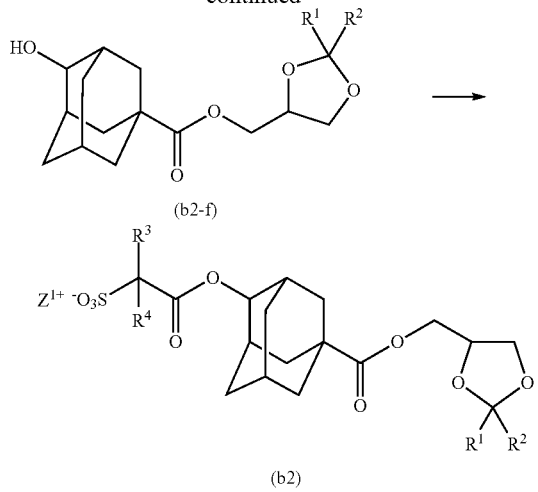

A salt represented by the formula (b3):

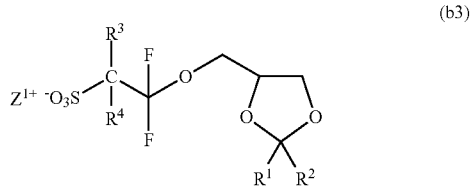

wherein $R^1$, $R^2$, $R^4$ and $Z^{1+}$ are the same as defined above, can be produced by reacting a salt represented by the formula (b3-a) with a compound represented by the formula (b3-b). The salt represented by the formula (b3-a) can be produced, for example, according to the method described in JP 2008-260745 A. Examples of the compound represented by the formula (b3-b) include acetone, cyclohexaneone and adamantanone.

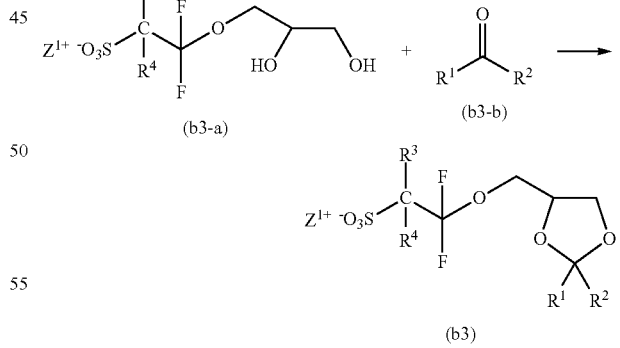

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount.

Preferable examples of the acid generator other than SALT (I) include salts represented by the formulae (B1-1) to (B1-17), the salt containing a triphenylsulfoniumcation or a tri-tolysulfonium cation is more preferable, and the salts represented by the formulae (B1-1), (B1-2), (B1-3), (B1-6), (B1-7), (B1-11), (B1-12), (B1-13) and (B1-14) are especially preferable.

(B1-1)
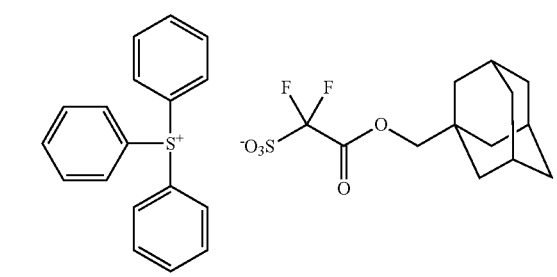

(B1-2)
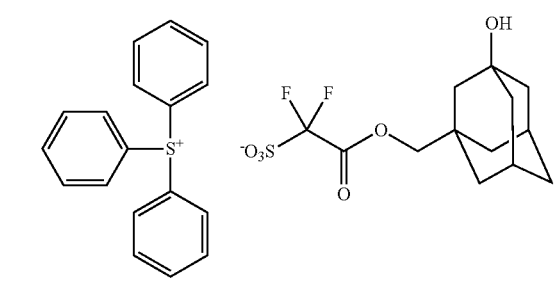

(B1-3)
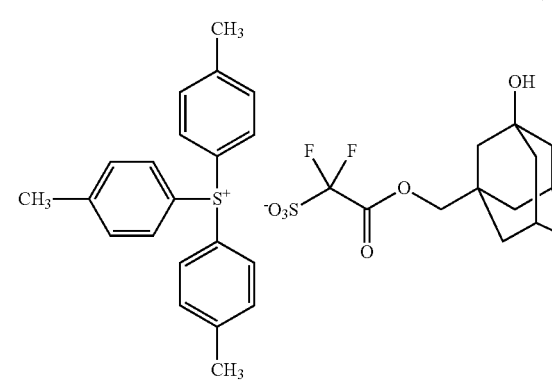

(B1-4)
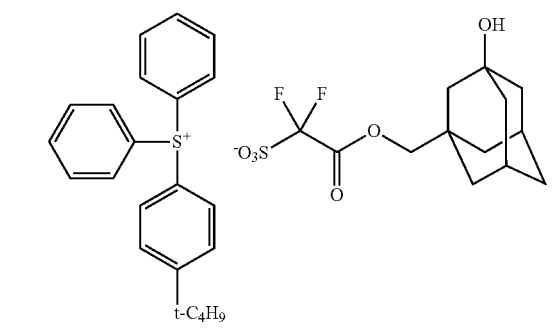

(B1-5)
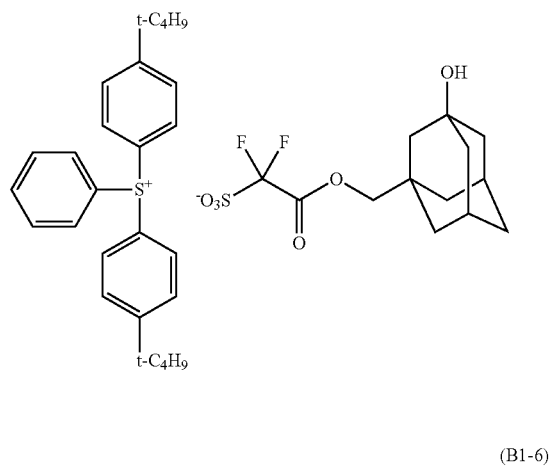

(B1-6)
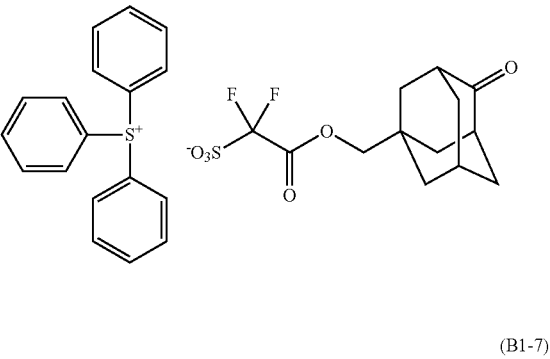

(B1-7)
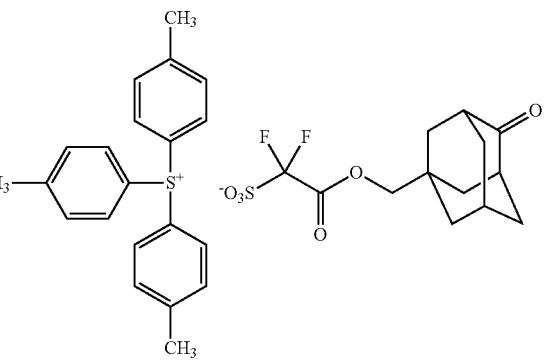

(B1-8)
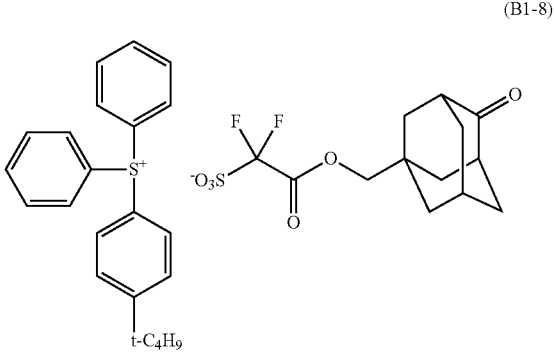

-continued (B1-9)
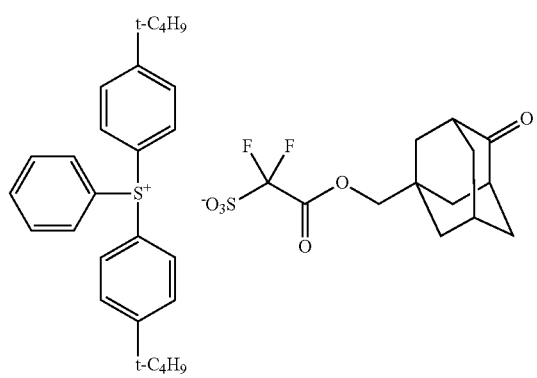

(B1-10)

(B1-14)
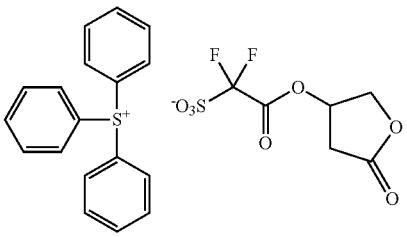

(B1-15)
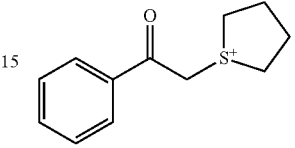
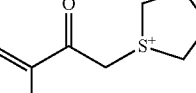 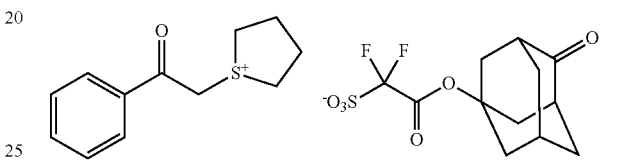

(B1-16)
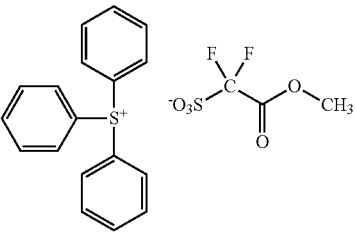

(B1-17)

(B1-11)
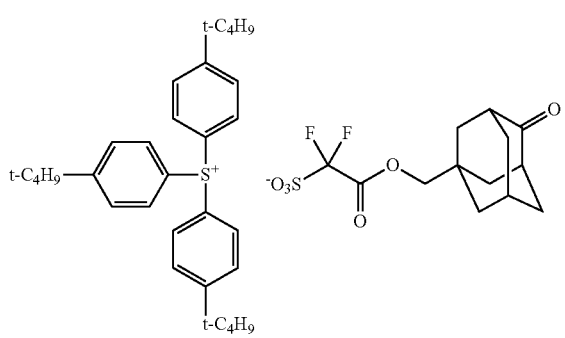

(B1-12)
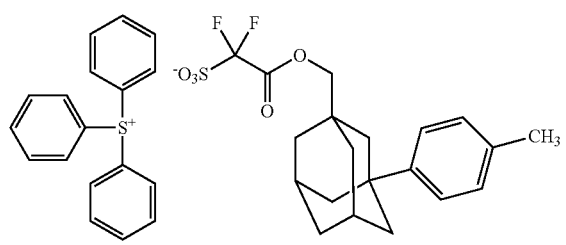

(B1-13)
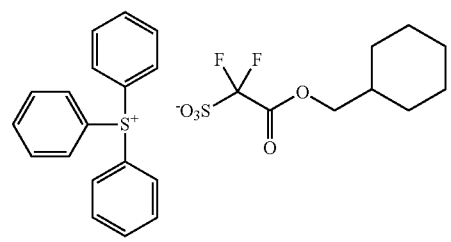

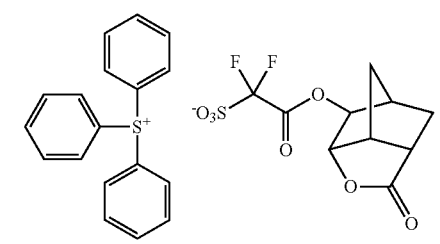

When the acid generator of the present invention contains SALT (I) and the acid generator other than SALT (I), the content of SALT (I) is preferably 10 parts by mass or more and more preferably 30 parts by mass or more per 100 parts by mass of the acid generator of the present invention, and the content of SALT (I) is preferably 90 parts by mass or less and more preferably 70 parts by mass or less per 100 parts by mass of the acid generator of the present invention.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

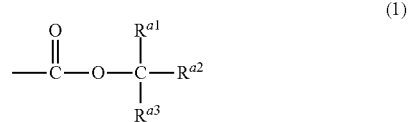

(1)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ can be bonded each other to form a C3-C21 ring together with a carbon atom to which $R^{a1}$ and $R^{a2}$ are bonded.

Examples of the alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

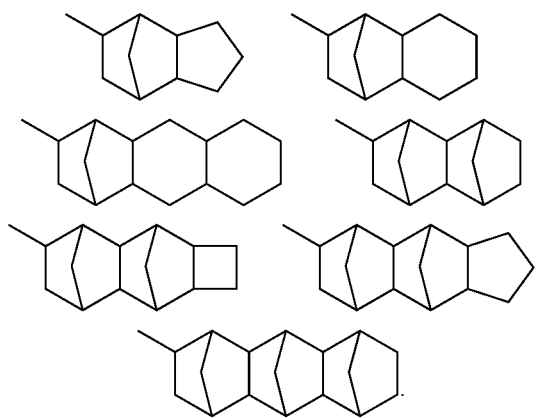

The alicyclic hydrocarbon group preferably has 5 to 16 carbon atoms.

Examples of the ring formed by bonding $R^{a1}$ and $R^{a2}$ each other include the following groups and the ring preferably has 4 to 13 carbon atoms.

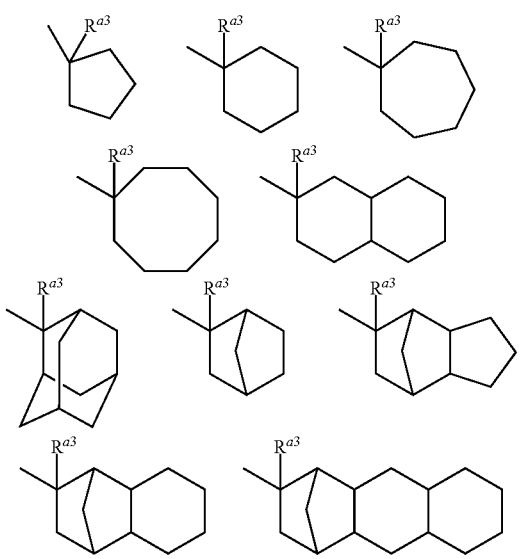

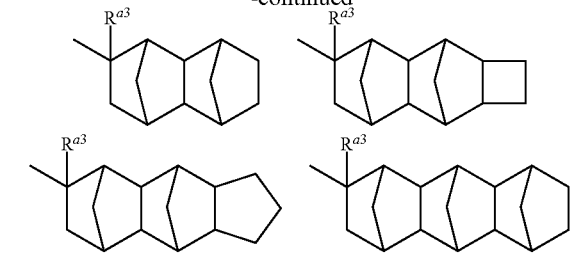

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the acid-labile group include a group represented by the formula (20):

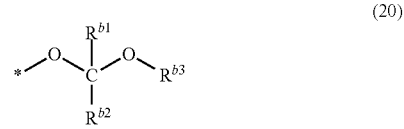

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C21 ring together with the carbon atom and the oxygen atom to which they are bonded, and one or more —$CH_2$— in the hydrocarbon group and the ring can be replaced by —O— or —S—.

The group represented by the formula (20) has an acetal structure.

Examples of the hydrocarbon group include an alkyl group, an alicyclic hydrocarbon group and an aromatic hydrocarbon group. Examples of the alkyl group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

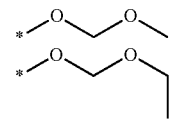

-continued

[Chemical structures shown]

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded in its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the compound having an acid-labile group include monomers represented by the formulae (a1-1) and (a1-2):

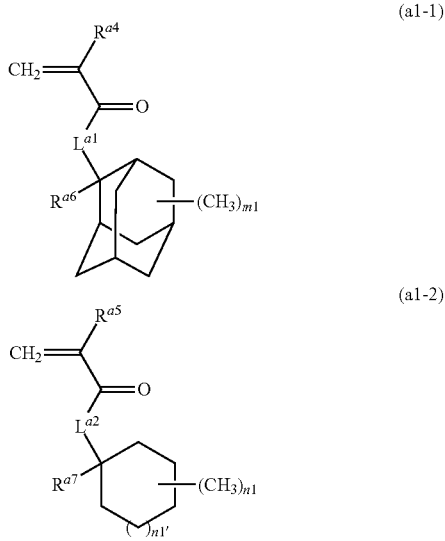

(a1-1)

(a1-2)

wherein $R^{a4}$ and $R^{a5}$ each independently represents a hydrogen atom or a methyl group, $R^{a6}$ and $R^{a7}$ each independently represents a C1-C8 alkyl group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 or 1.

The alkyl group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the alkyl group include a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the alicyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{k1}$—CO—O— in which * represents a binding position to —CO—, and k1 represents an integer of 1 to 4, and k1 is more preferably 1. $L^{a1}$ is preferably *—O—. $L^{a2}$ is preferably *—O— or *—O—$(CH_2)_{k1}$—CO—O— in which * represents a binding position to —CO—, and k1 is the same as defined above, and k1 is more preferably 1. $L^{a2}$ is preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include those described in JP 2010-204646 A. The monomers represented by the formulae (a1-1-1) to (a1-1-6) are preferable, and the monomers represented by the formulae (a1-1-1) to (a1-1-3) are more preferable.

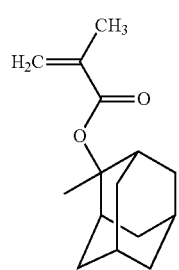
(a1-1-1)

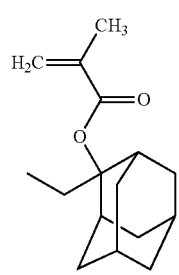
(a1-1-2)

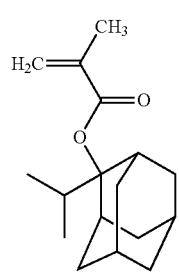
(a1-1-3)

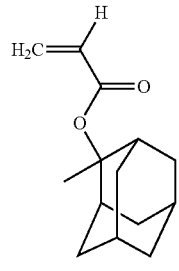
(a1-1-4)

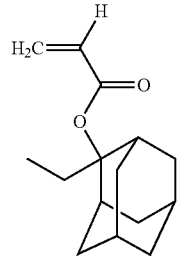
(a1-1-5)

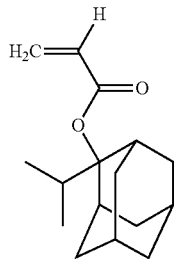
(a1-1-6)

Examples of the monomers represented by the formula (a1-2) include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, and the monomers represented by the formulae (a1-2-1) to (a1-2-6) are preferable and the following monomers represented by the formulae (a1-2-3) to (a1-2-4) are more preferable, and the monomer represented by the formula (a1-2-3) is especially preferable.

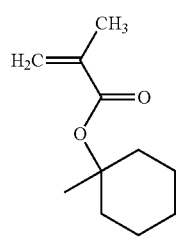
(a1-2-1)

(a1-2-2)

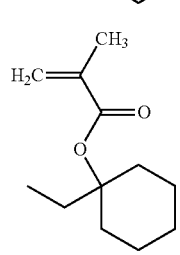
(a1-2-3)

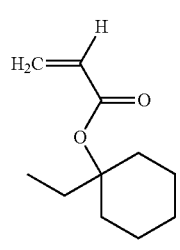
(a1-2-4)

(a1-2-5)

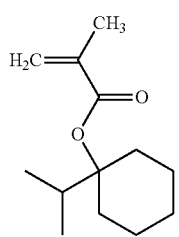

(a1-2-6)

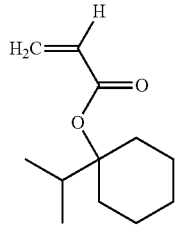

(a2-0)

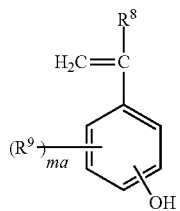

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

(a2-1)

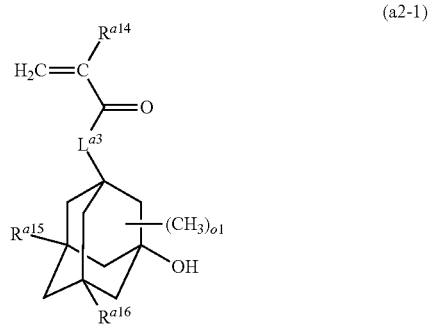

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength:248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength:193 nm) is used as an exposure system, the resin containing the structural unit derived from the monomer represented by the formula (a2-1) is preferable.

In the formula (a2-0), examples of the halogen atom include a fluorine atom. Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy The content of the structural unit derived from a monomer having an acid-labile group in the resin is usually 10 to 95% by mole, preferably 15 to 90% by mole and more preferably 20 to 85% by mole based on 100% by mole of all the structural units of the resin. When the resin contains the structural unit derived from the monomer represented by the formula (a1-1) or (a1-2), the content of the structural unit derived from the monomer represented by the formula (a1-1) or (a1-2) in the resin is usually 10 to 80% by mole, preferably 20 to 60% by mole based on 100% by mole car all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the monomers described in JP 2010-204634 A, and 4-hydroxyatyrene and 4-hydroxy-α-methylstyrene are preferable.

The content of the structural unit derived from the monomer represented by the formula (a2-0) is usually 0 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include the monomers described in JP 2010-204646 A, and the monomers represented by the formulae (a2-1-1) to (a2-1-6) are preferable, and the monomers represented by the formulae (a2-1-1) to (a2-1-4) are more preferable, and the monomers represented by the formulae (a2-1-1) and (a2-1-3) are still more preferable,

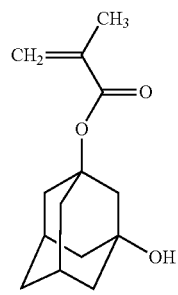

(a2-1-1)

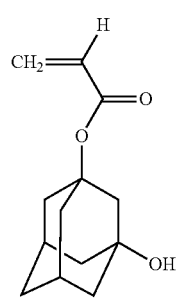

(a2-1-2)

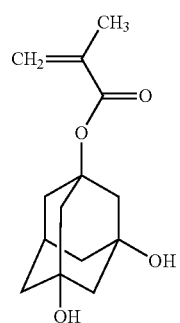

(a2-1-3)

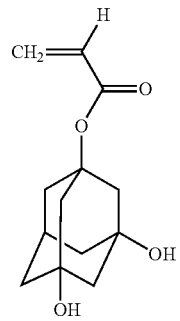

(a2-1-4)

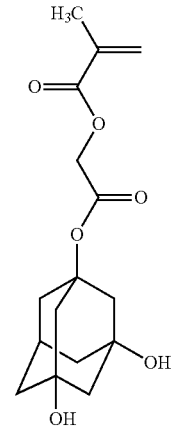

(a2-1-5)

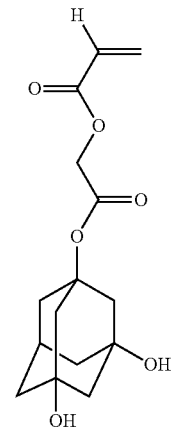

(a2-1-6)

When the resin contains the structural unit derived from the monomer represented by the formula (a2-1), the content of the structural unit derived from the monomer represented by the formula (a2-1) is usually 3 to 40% by mole based on total molar of all the structural units of the resin, and preferably 5 to 35% by mole and more preferably 5 to 30% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

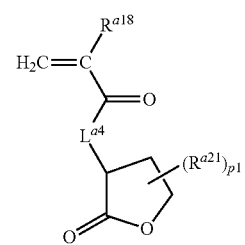
(a3-1)

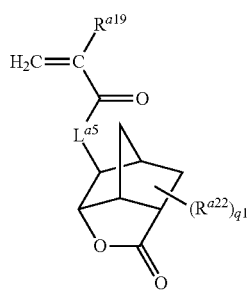
(a3-2)

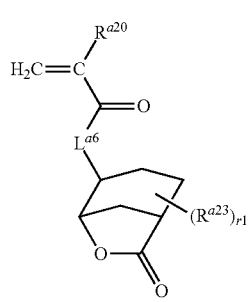
(a3-3)

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 4, and it is more preferred that $L^{a4}$, $L^{a5}$ and $L^{a6}$ are *—O— or *—O—$CH_2$—CO—O—. It is still more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the monomers described in JP 2010-204646 A, and the monomers represented by the formulae (a3-1-1) to (a3-1-4), (a3-2-1) to (a3-2-4) and (a3-3-1) to (a3-3-4) are preferable, and the monomers represented by the formulae (a3-1-1) to (a3-1-2) and (a3-2-3) to (a3-2-4) are more preferable, and the monomers represented by the formulae (a3-1-1) and (a3-2-3) are still more preferable.

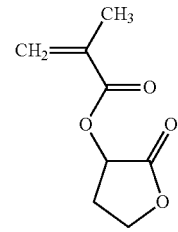
(a3-1-1)

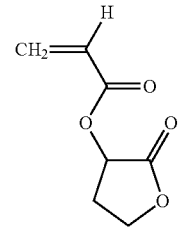
(a3-1-2)

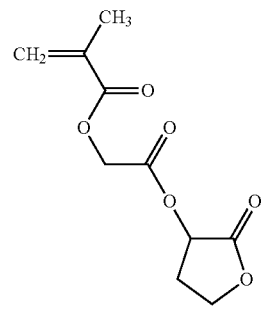
(a3-1-3)

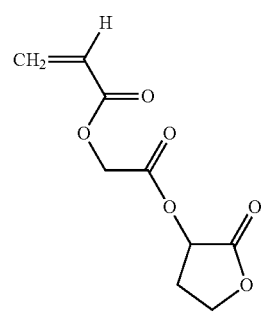
(a3-1-4)

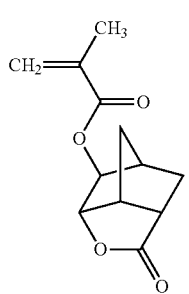
(a3-2-1)

(a3-2-2) 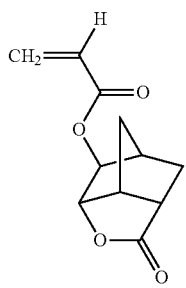

(a3-2-3) 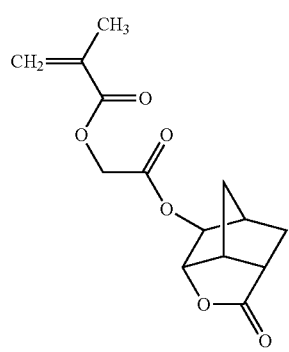

(a3-2-4) 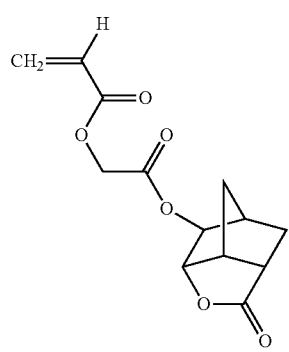

(a3-3-1) 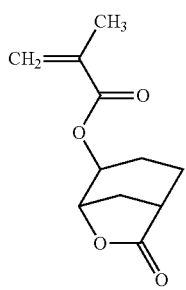

(a3-3-2) 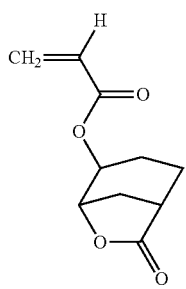

(a3-3-3) 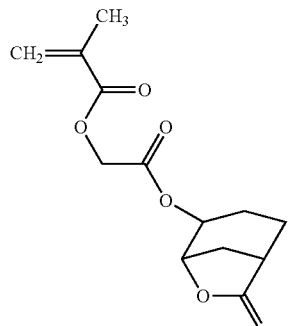

(a3-3-4) 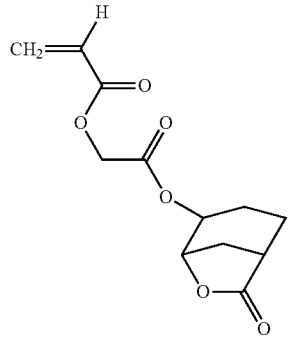

When the resin contains the structural unit derived from the monomer having no acid-labile group and having a lactone ring, the content thereof is usually 5 to 60% by mole based on total molar of all the structural units of the resin, and preferably 10 to 55% by mole, more preferably 10 to 50% by mole, and especially preferably 15 to 50% by mole.

The resin can contain one or more structural units derived from the monomers other than the above-mentioned monomers.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1) The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The content of the acid generator is usually 1 part by mass or more per 100 parts of the resin, and preferably 3 parts by mass or more. The content of the acid generator is usually 40 parts by mass or less per 100 parts of the resin, and preferably 35 parts by mass or less.

The content of the resin is usually 80% by mass or more and 99% by mass or less based on sum of solid component. In this specification, "solid component" means components other than solvent in the photoresist composition.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

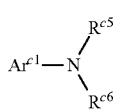

(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

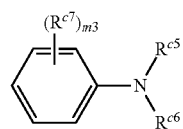

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3)

(C4)

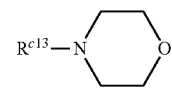

(C5)

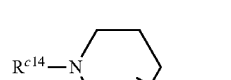

(C6)

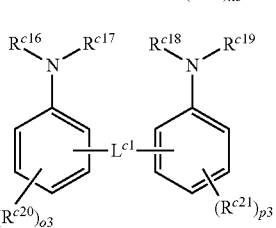

(C7)

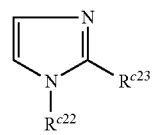

(C8)

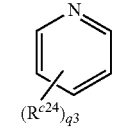

(C9)

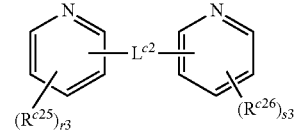

(C10)

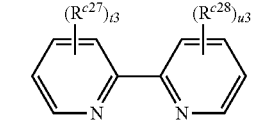

(C11)

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{16}$ to $R^{19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, trimethylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole Examples of the amine represented by the formula (C9) include pyridine and 4-methylpyridine. Examples of the amine represented by the formula (C10) include di-2-pyridyl ketone, 1,2-di(2-pyridyl) ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 5% by mass based on sum of solid component, preferably 0.01 to 3% by mass and more preferably 0.01 to 1% by mass.

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by mass or more, preferably 92% by mass or more preferably 94% by mass or more based on total amount of the photoresist composition of the present invention. The amount of the solvent is usually 99.9% by mass or less and preferably 99% by mass or less based on total amount of the photoresist composition of the present invention.

The photoresist compositions of the present invention can contain, if necessary, a small amount of various additives such as a sensitizer, a dissolution inhibitor, otherpolymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on amass basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material manufactured by TOSOH CORPORATION. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Example 1

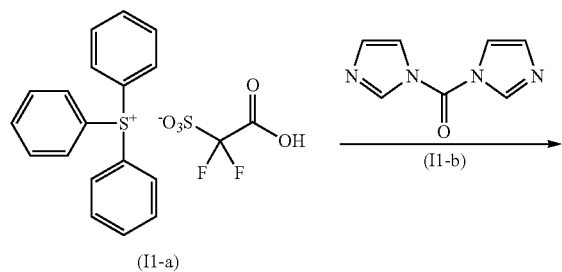

(I1-a)

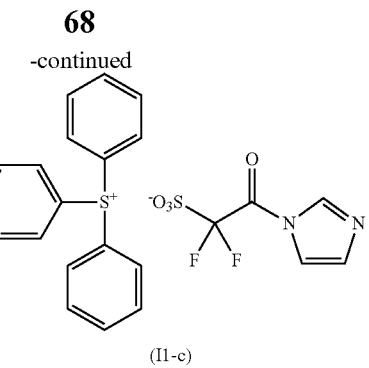

(I1-c)

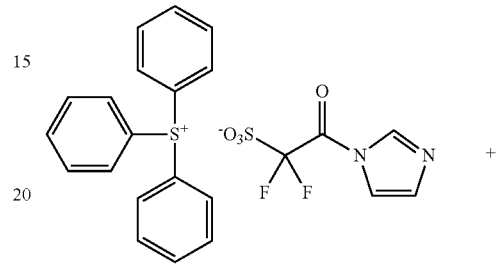

(I1-c)

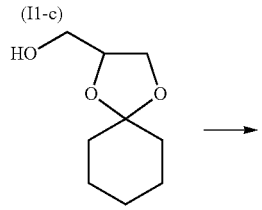

(I1-d)

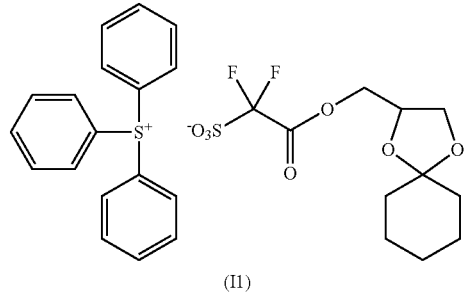

(I1)

The salt represented by the formula (I1-a) was prepared according to the method described in JP 2008-127367 A.

A mixture of 5.00 parts of the salt represented by the formula (I1-a) and 25 parts of chloroform was stirred at 30° C. for 30 minutes. To the mixture, 1.83 parts of the compound represented by the formula (I1-b) was added, and the resultant mixture was stirred at 60° C. for 1 hour to obtain a solution containing a compound represented by the formula (I1-c). To the solution obtained, 1.76 parts of a compound represented by the formula (I1-d) was added and the resultant mixture was stirred at 23° C. for 3 hours. The reaction mixture obtained was mixed with 10 parts of ion-exchanged water to stir and separate. The organic layer obtained was washed five times with water. To the organic layer, 1.00 part of active carbon was added to stir at 23° C. for 30 minutes followed by filtration. The filtrate obtained was concentrated. To the residue obtained, 30 parts of tert-butyl methyl ether was added. The resultant mixture was stirred, and the supernatant was removed. The residue obtained was dissolved in acetonitrile. The solution obtained was concentrated. The residue obtained was mixed with 20 parts og tert-butyl methyl ether. The resultant mixture was stirred, and the supernatant was removed. The residue obtained was dissolved in chloroform. The solution obtained was concentrated to obtain 2.19 parts of a salt represented by the formula (I1). This is called as Salt I1.

MS (ESI(+) Spectrum): M⁺ 263.1
MS (ESI(−) Spectrum): M⁻ 329.1

Example 2

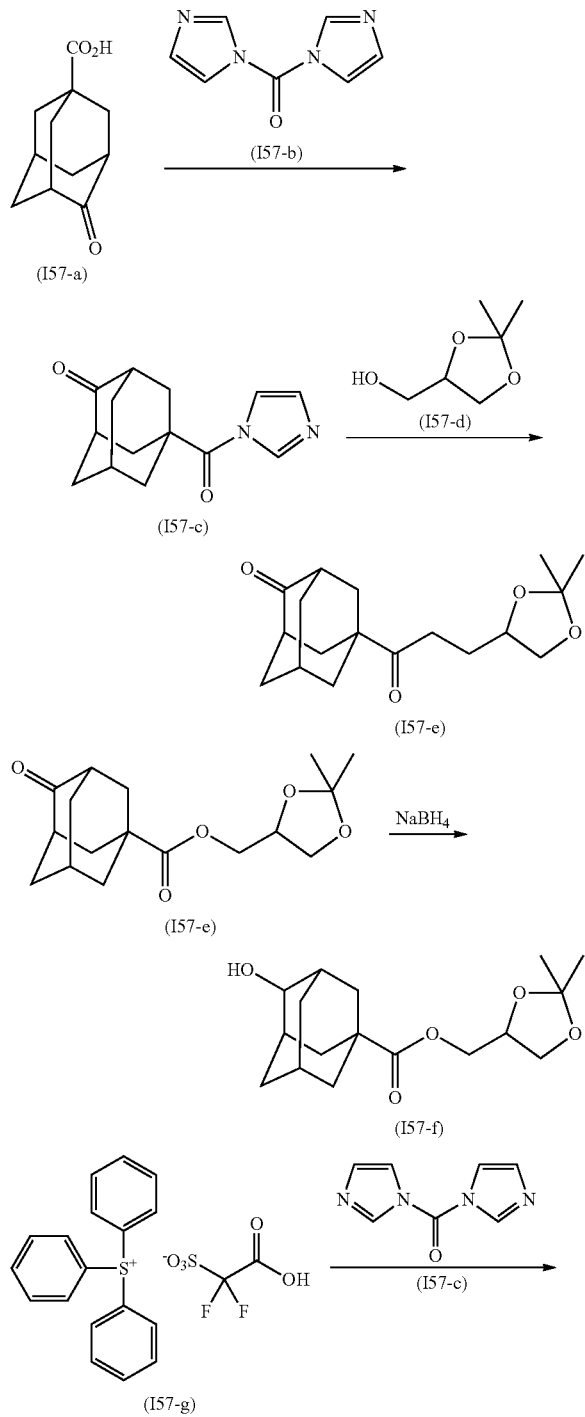

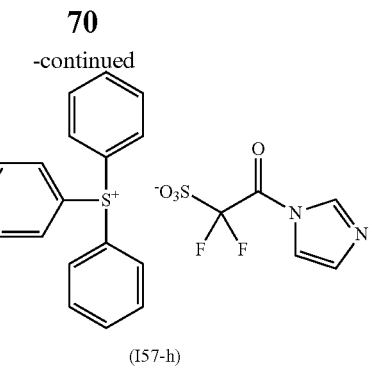

A mixture of 6.00 parts of the compound represented by the formula (I57-a) and 30 parts of chloroform was stirred at 23° C. for 30 minutes. To the mixture obtained, 5.51 parts of the compound represented by the formula (I57-b) was added, and the resultant mixture was stirred at 60° C. for 1 hour to obtain a solution containing a compound represented by the formula. (I57-c). After cooling down to 23° C., a solution containing 3.67 parts of the compound represented by the formula (I57-d) and 3.67 parts of chloroform was added dropwise over 30 minutes to the solution obtained. The resultant mixture was stirred at 23° C. for 12 hours. The mixture obtained was mixed with 15 parts of ion-exchanged water to stir and separate. The organic layer obtained was washed three times with water. The organic layer was filtrated and the filtrate obtained was concentrated to obtain 6.12 parts of the salt represented by the formula (I57-e)

A mixture of 5.00 parts of the compound represented by the formula (I57-e) and 27.85 parts of acetonitrile was stirred at 23° C. for 30 minutes. The mixture was cooled down to 0° C., and then, a mixture of 0.31 part of sodium borohydride and 3.07 parts of ion-exchanged water was added dropwise thereto over 10 minutes. The mixture obtained was stirred at 0° C. for 2 hours. To the reaction mixture obtained, 8.11 parts of 1N hydrochloric acid was added. The resultant mixture was stirred at 23° C. for 30 minutes followed by concentrating. The concentrate obtained was mixed with 44.56 parts of chloroform and 11.14 parts of ion-exchanged water to conduct separation. The organic layer was washed three times with water. The organic layer was filtrated and the filtrate obtained was concentrated. To the residue obtained, 37.70 parts of heptane was added, and the supernatant was removed. The residue obtained was dissolved in chloroform. The solution obtained was concentrated to obtain 3.27 parts of a compound represented by the formula (I57-f).

The salt represented by the formula (I57-g) was prepared according to the method described in JP 2008-127367 A.

A mixture of 3.87 parts of the salt represented by the formula (I57-g) and 19.41 parts of acetonitrile was stirred at 30° C. for 30 minutes. To the mixture, 1.71 parts of the compound represented by the formula (I57-c) was added, and the resultant mixture was stirred at 80° C. for 1 hour to obtain a solution containing a compound represented by the formula (I57-h). After the solution obtained was cooled down to 23° C., a mixture of 3.27 parts of a compound represented by the formula (I57-f) and 3.27 parts of acetonitrile was added to the solution. The resultant mixture was stirred at 80° C. for 12 hours. The reaction mixture obtained was concentrated, and the residue obtained was mixed with 28.82 parts of chloroform and 9.70 parts of ion-exchanged water to stir and separate. The organic layer obtained was washed five times with water. To the organic layer, 1.00 part of active carbon was added to stir at 23° C. for 30 minutes followed by filtration. The filtrate obtained was concentrated. To the residue obtained, 37.90 parts of tert-butyl methyl ether was added. The resultant mixture was stirred, and the supernatant was removed. The residue obtained was dissolved in acetonitrile. The solution obtained was concentrated. The residue obtained was mixed with 1.84 parts of acetonitrile and 27.60 parts of tert-butyl methyl ether. The resultant mixture was stirred, and the supernatant was removed. The residue obtained was dissolved in chloroform. The solution obtained was concentrated to obtain 2.96 parts of a salt represented by the formula (I57). This is called as Salt 157.

MS (ESI(+) Spectrum): M$^+$ 263.1

MS (ESI(−) Spectrum): M$^−$ 467.1

Example 3

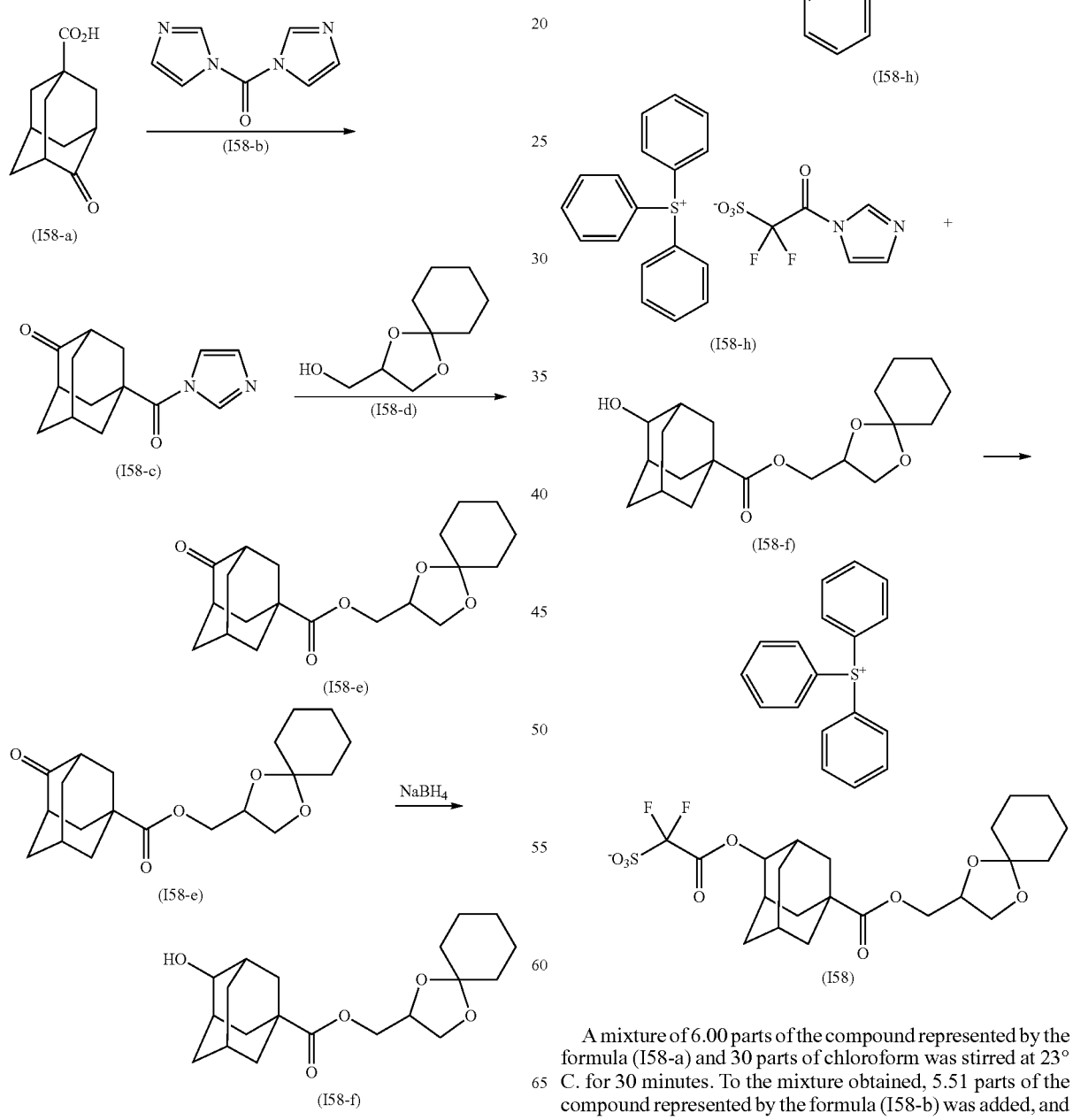

A mixture of 6.00 parts of the compound represented by the formula (I58-a) and 30 parts of chloroform was stirred at 23° C. for 30 minutes. To the mixture obtained, 5.51 parts of the compound represented by the formula (I58-b) was added, and the resultant mixture was stirred at 60° C. for 1 hour to obtain a solution containing a compound represented by the formula (I58-c). After cooling down to 23° C., a solution containing 4.78 parts of the compound represented by the formula (I58-d) and 4.78 parts of chloroform was addeddropwise over 30 minutes to the solution obtained. The resultant mixture was stirred at 23° C. for 12 hours. The mixture obtained was mixed with 15 parts of ion-exchanged water to stir and separate. The organic layer obtained was washed three times with water. The organic layer was filtrated and the filtrate obtained was concentrated to obtain 6.28 parts of the salt represented by the formula (I58-e).

A mixture of 5.65 parts of the compound represented by the formula (I58-e) and 31.47 parts of acetonitrile was stirred at 23° C. for 30 minutes. The mixture was cooled down to 0° C., and then, a mixture of 0.31 part of sodium borohydride and 3.07 parts of ion-exchanged water was added dropwise thereto over 10 minutes. The mixture obtained was stirred at 0° C. for 2 hours. To the reaction mixture obtained, 8.11 parts of 1N hydrochloric acid was added. The resultant mixture was stirred at 23° C. for 30 minutes followed by concentrating. The concentrate obtained was mixed with 48.32 parts of chloroform and 12.08 parts of ion-exchanged water to conduct separation. The organic layer was washed three times with water. The organic layer was filtrated and the filtrate obtained was concentrated. To the residue obtained, 39.12 parts of heptane was added, and the supernatant was removed. The residue obtained was dissolved in chloroform. The solution obtained was concentrated to obtain 3.85 parts of a compound represented by the formula (I58-f).

The salt represented by the formula (I58-g) was prepared according to the method described in JP 2008-127367 A. A mixture of 3.87 parts of the salt represented by the formula (I58-g) and 19.41 parts of acetonitrile was stirred at 30° C. for 30 minutes. To the mixture, 1.71 parts of the compound represented by the formula (I58-c) was added, and the resultant mixture was stirred at 80° C. for 1 hour to obtain a solution containing a compound represented by the formula (I58-h). After the solution obtained was cooled down to 23° C., a mixture of 3.69 parts of a compound represented by the formula (I58-f) and 3.69 parts of acetonitrile was added to the solution. The resultant mixture was stirred at 80° C. for 12 hours. The reaction mixture obtained was concentrated, and the residue obtained was mixed with 42.22 parts of chloroform and 10.56 parts of ion-exchanged water to stir and separate. The organic layer obtained was washed five times with water. To the organic layer, 1.00 part of active carbon was added to stir at 23° C. for 30 minutes followed by filtration. The filtrate obtained was concentrated. To the residue obtained, 28.40 parts of tert-butyl methyl ether was added. The resultant mixture was stirred, and the supernatant was removed. The residue obtained was dissolved in acetonitrile. The solution obtained was concentrated. The residue obtained was mixed with 1.91 parts of acetonitrile and 28.68 parts of tert-butyl methyl ether. The resultant mixture was stirred, and the supernatant was removed. The residue obtained was dissolved in chloroform. The solution obtained was concentrated to obtain 2.68 parts of a salt represented by the formula (I58). This is called as Salt 158.

MS (ESI(+) Spectrum): M⁺ 263.1
MS (ESI(−) Spectrum): M⁻ 507.2

Example 4

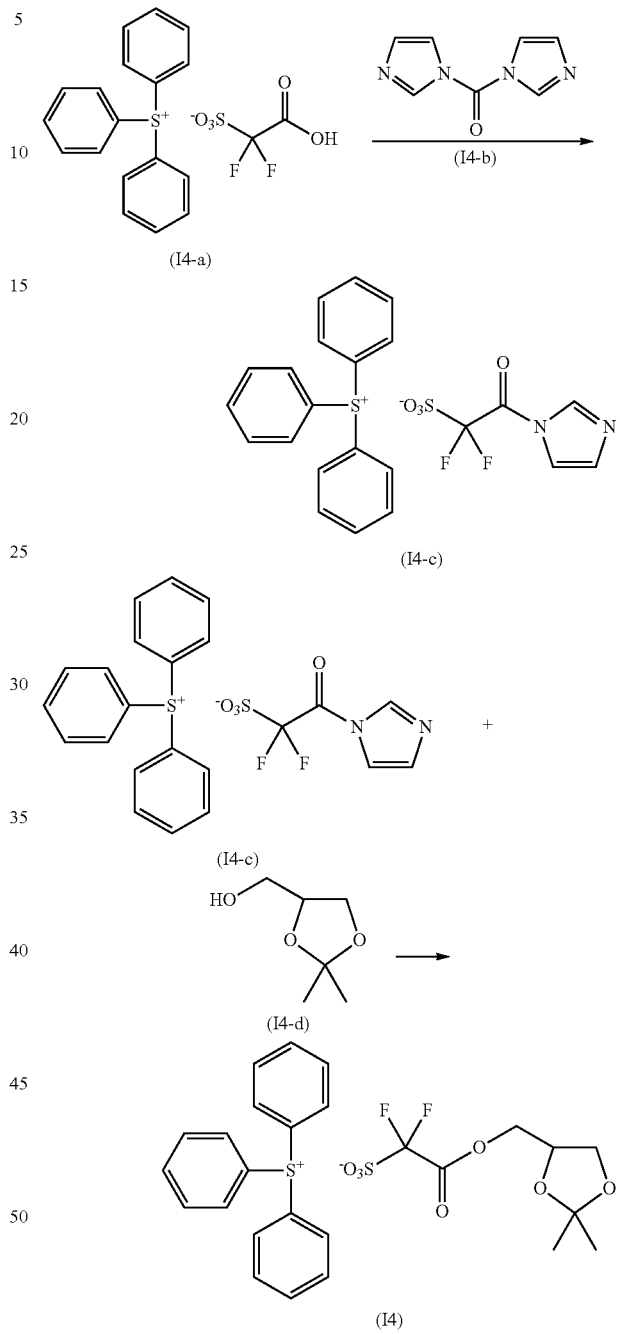

The salt represented by the formula (I4-a) was prepared according to the method described in JP 2008-127367 A.

A mixture of 20.00 parts of the salt represented by the formula (I4-a) and 100 parts of chloroform was stirred at 30° C. for 30 minutes. To the mixture, 8.81 parts of the compound represented by the formula (I4-b) was added, and the resultant mixture was stirred at 60° C. for 1 hour to obtain a solution containing a compound represented by the formula (I4-c). To the solution obtained, 6.00 parts of a compound represented by the formula (I4-d) and 6.00 parts of chloroform were added and the resultant mixture was stirred at 23° C. for 3 hours. The reaction mixture obtained was mixed with 25 parts of ion-exchanged water to stir and separate. The organic layer obtained was washed five times with water. To the organic layer, 1.00 part of active carbon was added to stir at 23° C. for 30 minutes followed by filtration. The filtrate obtained was concentrated. To the residue obtained, 120 parts of tert-butyl methyl ether was added. The resultant mixture was stirred and then, filtrated to obtain 20.71 parts of a salt represented by the formula (I4). This is called as Salt I1.

MS (ESI(+) Spectrum): $M^+$ 263.1
MS (ESI(−) Spectrum): $M^-$ 289.0

Example 5

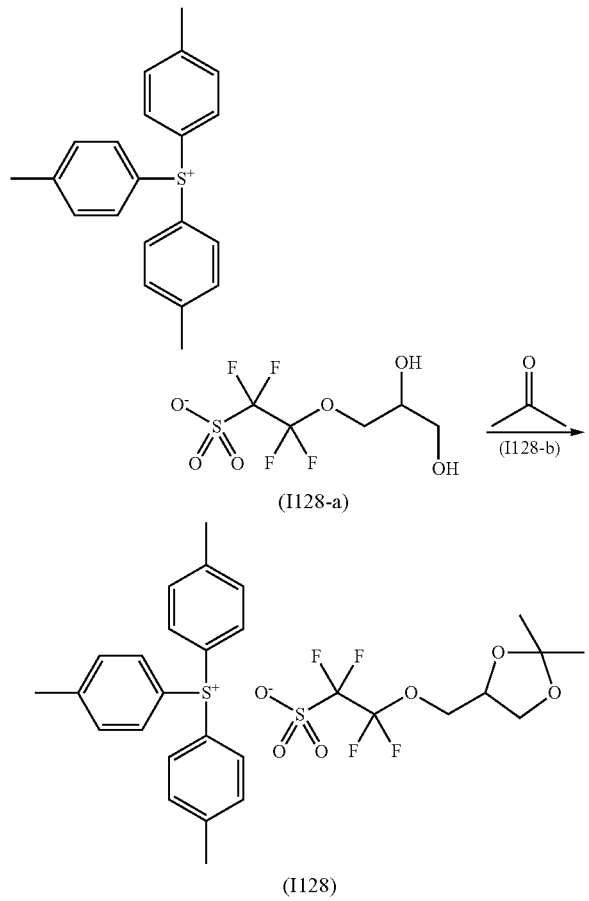

(I128)

solved in acetonitrile. The solution obtained was concentrated. To the residue obtained, 20 parts of tert-butyl methyl ether was added. The resultant mixture was stirred and then, the supernatant was removed. The residue obtained was dissolved in chloroform. The solution obtained was concentrated to obtain 1.59 parts of a salt represented by the formula (I128). This is called as Salt I128.

MS (ESI(+) Spectrum): $M^+$ 305.1
MS (ESI(−) Spectrum): $M^-$ 311.0

Example 6

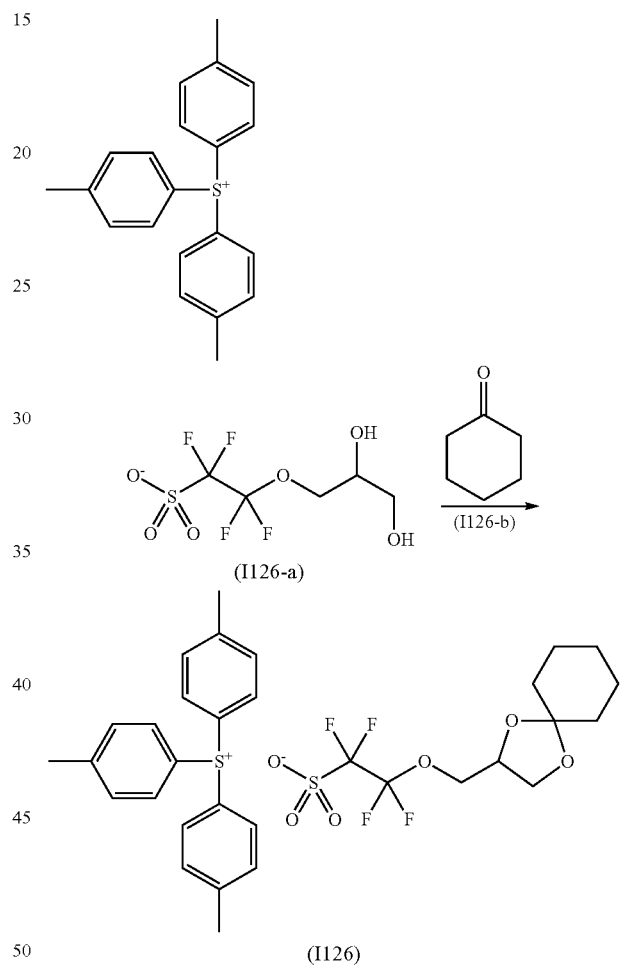

(I126)

The salt represented by the formula (I128-a) was prepared according to the method described in JP 2008-260745 A.

A mixture of 1.69 parts of the salt represented by the formula (I128-a), 60 parts of the compound represented by the formula (I128-b) and 0.03 part of concentrated sulfuric acid was refluxed with dehydration at 60° C. for 24 hours. The mixture obtained was cooled down to 23° C. The mixture was mixed with 120 parts of chloroform and 16.16 parts of 1% aqueous potassium carbonate solution followed by conducting separation. The organic layer obtained was mixed with 40 parts of ion-exchanged water followed by separation. The organic layer obtained was washed five times with water. To the organic layer, 1.00 part of active carbon was added to stir at 23° C. for 30 minutes followed by filtration. The filtrate obtained was concentrated. The residue obtained was dis- The salt represented by the formula (I126-a) was prepared according to the method described in JP 2008-260745 A.

A mixture of 1.69 parts of the salt represented by the formula (I126-a), 10 parts of the compound represented by the formula (I126-b), 120 parts of chloroform and 0.03 part of concentrated sulfuric acid was refluxed with dehydration at 65° C. for 48 hours. The mixture obtained was cooled down to 23° C. The mixture was mixed with 16.16 parts of 1% aqueous potassium carbonate solution followed by conducting separation. The organic layer obtained was mixed with 40 parts of ion-exchanged water followed by separation. The organic layer obtained was washed five times with water. To the organic layer, 1.00 part of active carbon was added to stir at 23° C. for 30 minutes followed by filtration. The filtrate obtained was concentrated. The residue obtained was dissolved in acetonitrile. The solution obtained was concentrated. To the residue obtained, 20 parts of tert-butyl methyl ether was added. The resultant mixture was stirred and then, the supernatant was removed. The residue obtained was dissolved in chloroform. The solution obtained was concentrated to obtain 1.61 parts of a salt represented by the formula (I126). This is called as Salt I126.

MS (ESI(+) Spectrum): M$^+$ 305.1

MS (ESI(−) Spectrum): M$^−$ 351.1

Example 7

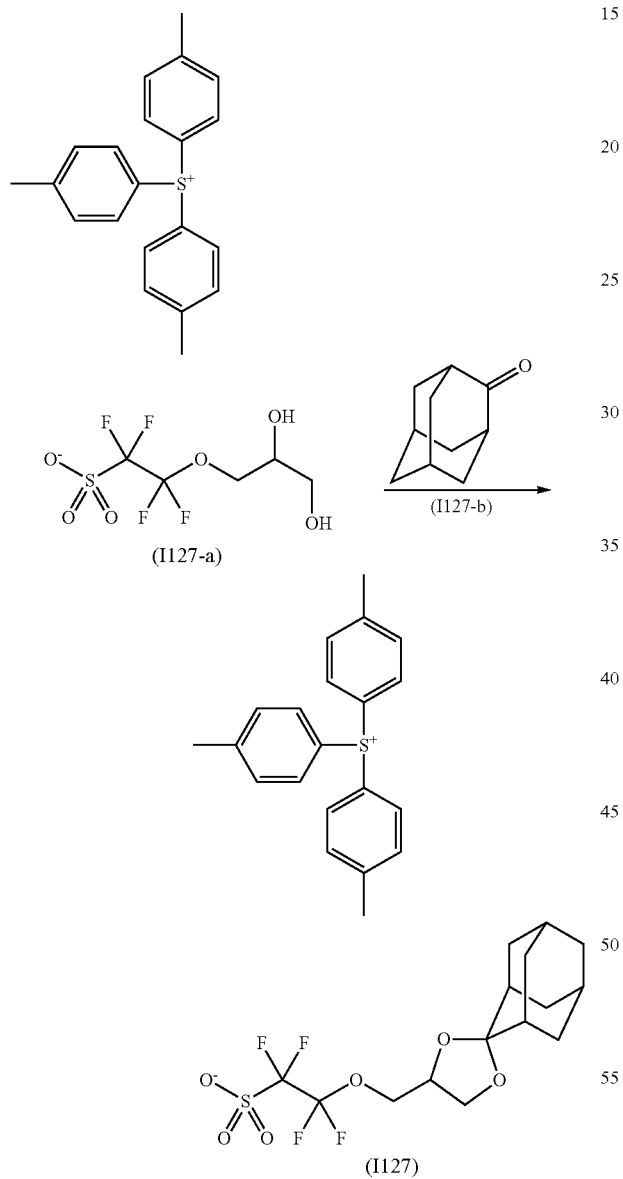

The salt represented by the formula (I127-a) was prepared according to the method described in JP 2008-260745 A.

A mixture of 1.69 parts of the salt represented by the formula (I1127-a), 10 parts of the compound represented by the formula (I127-b), 120 parts of chloroform and 0.03 part of concentrated sulfuric acid was refluxed with dehydration at 65° C. for 24 hours. The mixture obtained was cooled down to 23° C. The mixture was mixed with 16.16 parts of 1% aqueous potassium carbonate solution followed by conducting separation. The organic layer obtained was mixed with 40 parts of ion-exchanged water followed by separation. The organic layer obtained was washed five times with water. To the organic layer, 1.00 part of active carbon was added to stir at 23° C. for 30 minutes followed by filtration. The filtrate obtained was concentrated. The residue obtained was dissolved in acetonitrile. The solution obtained was concentrated. To the residue obtained, 20 parts of tert-butyl methyl ether was added. The resultant mixture was stirred and then, the supernatant was removed. The residue obtained was dissolved in chloroform. The solution obtained was concentrated to obtain 1.45 parts of a salt represented by the formula (I127). This is called as Salt I127.

MS (ESI(+) Spectrum): M$^+$ 305.1

MS (ESI(−) Spectrum): M$^−$ 403.1

Monomers used in the following Resin Synthesis Examples 1 to 2 are following monomers.

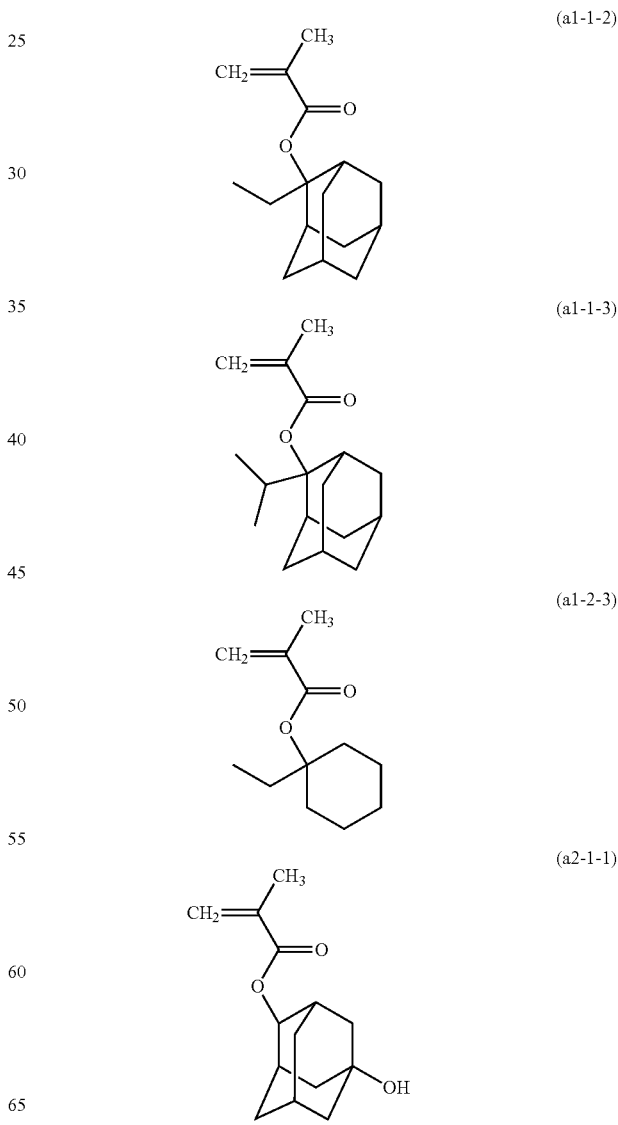

(a3-1-1)

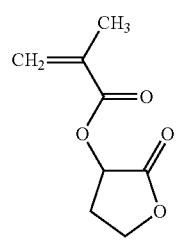

(a3-2-3)

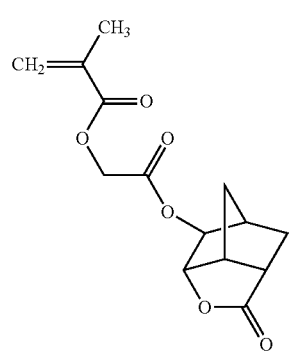

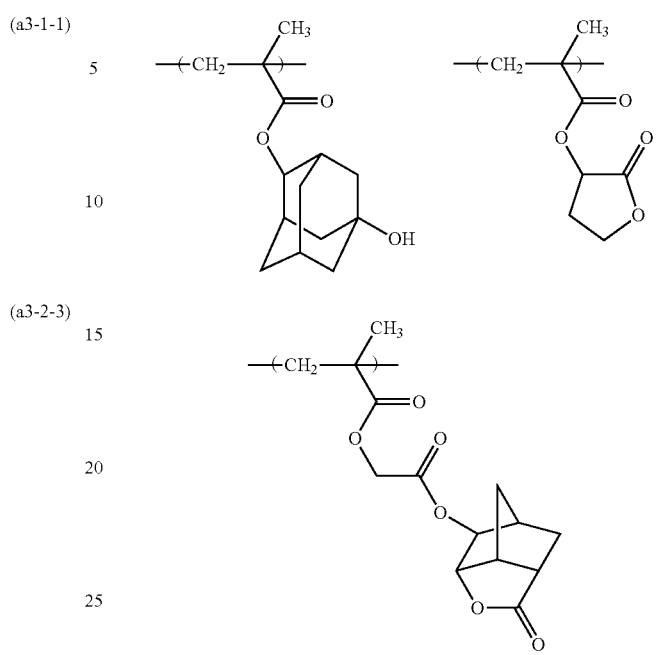

Resin Synthesis Example 1

The monomers (a1-1-3), (a1-2-3), (a2-1-1), (a3-1-1) and (a3-2-3) were mixed in a molar ratio of 30/14/6/20/30 (monomer (a1-1-3)/monomer (a1-2-3)/monomer (a2-1-1)/monomer (a3-1-1)/monomer (a3-2-3)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $8.1 \times 10^3$ was obtained in a yield of 65%. This resin is called as resin A1. Resin A1 had the followina structural units.

Resin Synthesis Example 2

The monomers (a1-1-2), (a2-1-1) and (a3-1-1) were mixed in a molar ratio of 50/25/25 (monomer (a1-1-2)/monomer (a2-1-1)/monomer (a3-1-1)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $9.2 \times 10^3$ was obtained in a yield of 60%. This resin is called as resin A2, Resin A2 had the following structural units.

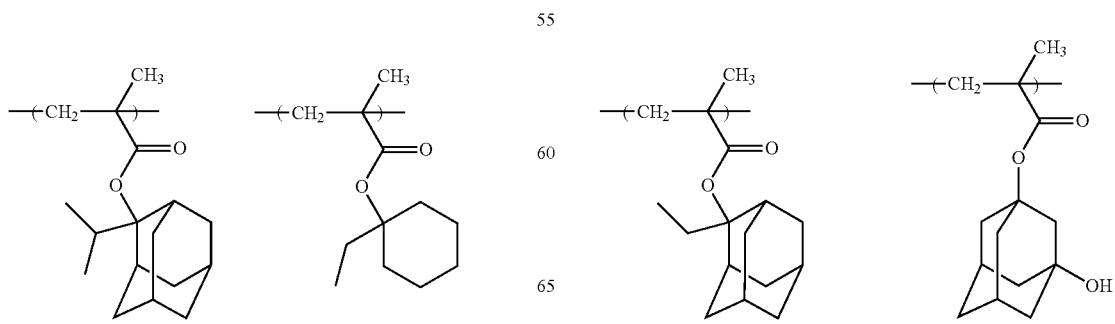

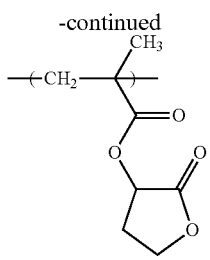

Examples 8 to 22 and Comparative Example 1

<Resin>
Resin. A1, A2
<Acid generator>
I1: Salt I1
I57: Salt I57
I58: Salt I58
I4: Salt I4
I128: Salt I128
I126: Salt I126
I127: Salt I127
B1:

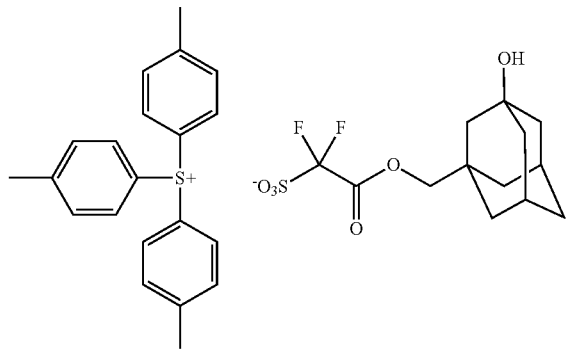

B2:

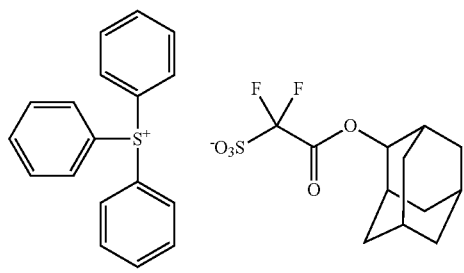

<Quencher>
C1: 2,6-diisopropylaniline
<Solvent>

| E1: | propylene glycol monomethyl ether acetate | 265 parts |
|---|---|---|
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 8)
Acid generator (kind and amount are described in Table 8)
Quencher (kind and amount are described in Table 8)
Solvent E1

TABLE 8

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 8 | A1/10 | I1/1.00 | C1/0.07 | 100 | 90 |
| Ex. 9 | A1/10 | I1/0.50 B1/0.50 | C1/0.07 | 100 | 90 |
| Ex. 10 | A2/10 | I1/0.50 B1/0.50 | C1/0.07 | 100 | 100 |
| Ex. 11 | A2/10 | I1/0.50 B2/0.50 | C1/0.07 | 100 | 100 |
| Ex. 12 | A1/10 | I1/1.00 | C1/0.07 | 100 | 90 |
| Ex. 13 | A1/10 | I57/1.00 | C1/0.07 | 100 | 90 |
| Ex. 14 | A1/10 | I58/1.00 | C1/0.07 | 100 | 90 |
| Ex. 15 | A1/10 | I1/0.50 B1/0.50 | C1/0.07 | 100 | 90 |
| Ex. 16 | A1/10 | I57/0.50 B1/0.50 | C1/0.07 | 100 | 90 |
| Ex. 17 | A1/10 | I58/0.50 B1/0.50 | C1/0.07 | 100 | 90 |
| Ex. 18 | A1/10 | I4/1.00 | C1/0.07 | 100 | 90 |
| Ex. 19 | A1/10 | I128/1.00 | C1/0.07 | 100 | 90 |
| Ex. 20 | A1/10 | I126/1.00 | C1/0.07 | 100 | 90 |
| Ex. 21 | A1/10 | I127/1.00 | C1/0.07 | 100 | 90 |
| Ex. 22 | A1/10 | I126/0.50 B1/0.50 | C1/0.07 | 100 | 90 |
| Comp. Ex. 1 | A2/10 | B2/1.00 | C1/0.07 | 100 | 100 |

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each pre-baked on a direct hotplate at a temperature shown in the column "PB" in Table 8 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise. Ultrapure water was used as an immersion medium.

After the exposure, each wafer was subjected to post-exposure baking on a hotplate at a temperature shown in the column "PEB" in Table 8 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 9.

Effective Sensitivity (ES): It was expressed as the amount of exposure that the line width of the line and space pattern of 50 nm became 1:1 after exposure through line and space pattern mask and development.

Line Edge Roughness (LER): The photoresist pattern at the amount of exposure that the line width of the photoresist pattern of 50 nm became 1:1 line and space pattern was as effective sensitivity was observed with a scanning electron microscope. The difference between the height of the highest point and height of the lowest point of the scabrous wall surface of the photoresist pattern was measured. When the difference is 3.5 nm or less, LER is very good and its evaluation is marked by "⊚⊚", when the difference is more than 3.5 nm and 4.0 nm or less, LER is good and its evaluation is marked by "⊚", when the difference is more than 4.0 nm and 5.0 nm or less, LER is usual its evaluation is marked by "◯", and when the difference is more than 5.0 nm, LER is bad and its evaluation is marked by "X". Further, each of the differences is also shown in parentheses in a column of "LER" in Table 9. The smaller the difference is, the better the pattern is.

TABLE 9

| Ex. No. | LER |
|---|---|
| Ex. 8 | ⊚ (3.51) |
| Ex. 9 | ⊚⊚ (3.43) |
| Ex. 10 | ◯ (4.02) |
| Ex. 11 | ◯ (4.47) |
| Ex. 12 | ⊚⊚ (3.38) |
| Ex. 13 | ⊚⊚ (3.24) |
| Ex. 14 | ⊚⊚ (3.16) |
| Ex. 15 | ⊚⊚ (3.33) |
| Ex. 16 | ⊚⊚ (3.18) |
| Ex. 17 | ⊚⊚ (3.12) |
| Ex. 18 | ⊚ (3.68) |
| Ex. 19 | ⊚ (3.74) |
| Ex. 20 | ⊚ (3.53) |
| Ex. 21 | ⊚ (3.52) |
| Ex. 22 | ⊚⊚ (3.28) |
| Comp. Ex. 1 | X (5.78) |

The salt of the present invention is suitable for an acid generator and the photoresist composition comprising the salt of the present invention provides a good photoresist pattern having good Line edge roughness.

What is claimed is:

1. A salt represented by the formula (I):

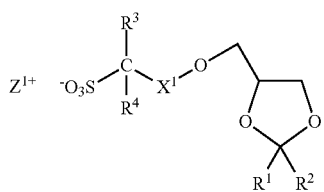

(I)

wherein $R^1$ and $R^2$ independently each represent a C1-C6 alkyl group or $R^1$ and $R^2$ are bonded each other to form a C5-C20 aliphatic ring together with the carbon atom to which they are bonded, $R^3$ and $R^4$ independently each represent a fluorine atom or a C1-C6 perfluoroalkyl group, $X^1$ represents a C1-C17 divalent saturated hydrocarbon group in which one or more —$CH_2$— can be replaced by —O— or —CO— and which may be substituted with one or more fluorine atoms, and $Z^{1+}$ represents an organic counter ion.

2. The salt according to claim 1, wherein the C5-C20 aliphatic ring formed by bonding $R^1$ and $R^2$ each other together with the carbon atom to which they are bonded is a cyclohexane ring.

3. The salt according to claim 1, wherein $X^1$ is *—CO— or a group represented by the following:

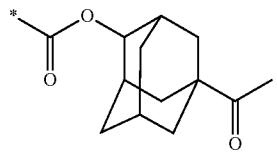 [SMILES: *C(=O)OC1C2CC3CC1CC(C(C)=O)(C3)C2]

wherein * represents a binding position to —$C(R^3)(R^4)$—.

4. The salt according to claim 1, wherein $Z^+$ is a triarylsulfonium cation.

5. An acid generator comprising the salt according to claim 1.

6. A photoresist composition comprising the acid generator according to claim 5 and a resin having an acid-labile group, being insoluble or poorly soluble in an aqueous alkali solution but becoming soluble in an aqueous alkali solution by the action of an acid.

7. The photoresist composition according to claim 6, which further comprises a basic compound.

8. A process for producing a photoresist pattern comprising the following steps (1) to (5)
   (1) a step of applying the photoresist composition according to claim 6 or 7 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

* * * * *